(12) United States Patent
Delcourt et al.

(10) Patent No.: US 9,193,978 B2
(45) Date of Patent: Nov. 24, 2015

(54) PRODUCTION OF ALKENES BY COMBINED ENZYMATIC CONVERSION OF 3-HYDROXYALKANOIC ACIDS

(75) Inventors: Marc Delcourt, Paris (FR); Maria Anissimova, Nozay (FR); Richard Tallon, Orsay (FR); Philippe Marlière, Mouscron (BE)

(73) Assignees: Scientist of Fortune, S.A., Luxembourg (LU); Global Bioenergies, Evry (FR)

( * ) Notice: Subject to any disclaimer, the term of this patent is extended or adjusted under 35 U.S.C. 154(b) by 0 days.

(21) Appl. No.: 13/880,042

(22) PCT Filed: Oct. 18, 2011

(86) PCT No.: PCT/EP2011/068174
§ 371 (c)(1),
(2), (4) Date: Jul. 6, 2013

(87) PCT Pub. No.: WO2012/052427
PCT Pub. Date: Apr. 26, 2012

(65) Prior Publication Data
US 2013/0316425 A1   Nov. 28, 2013

(30) Foreign Application Priority Data
Oct. 19, 2010   (EP) .................................. 10188001

(51) Int. Cl.
| | | |
|---|---|---|
| C12P 5/02 | (2006.01) | |
| C12N 1/20 | (2006.01) | |
| C12N 1/00 | (2006.01) | |
| C12N 1/12 | (2006.01) | |
| C07H 21/04 | (2006.01) | |
| C07K 1/00 | (2006.01) | |
| C12N 9/88 | (2006.01) | |

(52) U.S. Cl.
CPC ... C12P 5/02 (2013.01); C12N 9/88 (2013.01); C12Y 401/01033 (2013.01)

(58) Field of Classification Search
CPC .. C12N 15/117; C12N 2310/17; C12N 15/67; C12N 9/88; C12Y 401/01033; C12P 5/02
USPC ......... 435/167, 252.3, 252.33, 254.11, 257.2; 536/23.1, 23.2; 530/350
See application file for complete search history.

(56) References Cited

U.S. PATENT DOCUMENTS

2011/0165644 A1 *   7/2011   Marliere .................. 435/167

FOREIGN PATENT DOCUMENTS

| CA | 27229187 A1 * | 1/2010 | .............. C12P 5/02 |
|---|---|---|---|
| CN | 101044243 A | 9/2007 | |
| FR | WO 2010/001078 | 1/2010 | |
| JP | EP 0178153 | 4/1986 | |
| JP | EP 0205303 | 12/1986 | |
| WO | WO 02/099095 | 12/2002 | |
| WO | WO-2006/018211 | 2/2006 | |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Ladygina et al., A review on microbial synthesis of hydrocarbons. Process Biochem., 2006, vol. 41: 1001-1014.*
Poirier et al., Production of polyhydroxyalkanoates, a family of of biodegradable plastics and elastomers, in bacteria and plants. Biotechnology, 1995, vol. 13 (2): 142-150.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Byres, Emma et al., "Crystal Structures of Trypanosoma brucei and *Staphylococcus aureus* Mevalonate Diphoshate Decarboxylase Inform on the Determinants of Specificity and Reactivity," J. Mol. Biol (2007) 371: 540-553.
Dhe-Paganon, Sirano et. al., "Mechanisam of Mevalonate Pyrophosphate Decarboxylase: Evidence for a Carbocationic Transition State," Biochemistry (1994) 33: 13355-13362.
Huo, Xuewen and Viola, Ronald E. "Substrate Specificity and Identification of Function Groups of Homoserine Kinase from *Excherichia coli*," Biochemistry (1996) 35: 16180-16185.
Timson, David, "GHMP Kinases—Structures, Mechanisms, and Potential for Therapeutically Relevant Inhibition," Current Enzyme Inhibition (2007) 3: 77-94.
International Search Report received in PCT/EP2011/068174, Mar. 21, 2013.
Written Opinion dated Jan. 19, 2012 and received in PCT/EP2011/068174.

(Continued)

*Primary Examiner* — Ganapathirama Raghu
(74) *Attorney, Agent, or Firm* — Michele M. Wales; InHouse Patent Counsel, LLC

(57) ABSTRACT

The present invention relates to a method for generating alkenes through a biological process. More specifically, the invention relates to a method for producing alkenes (for example propylene, ethylene, 1-butylene, isobutylene or isoamylene) from molecules of the 3-hydroxyalkanoate type.

28 Claims, 13 Drawing Sheets

(56) References Cited

OTHER PUBLICATIONS

Figure 1:
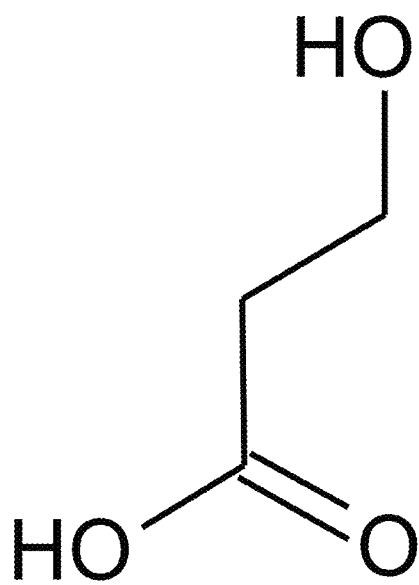

Written Opinion dated Feb. 11, 2013 and received in PCT/EP2011/068174.

Reply to Written Opinion dated Mar. 5, 2013 and filed in PCT/EP2011/068174.

IPER dated Mar. 21, 2013 and received in PCT/EP2011/068174.

Stinson, Robert A. et. al, "B-Alanine as an Ethylene Precursor. Investigations Towards Preparation, and Properties, of a Soluble Enzyme System from a Subcellular Particulate Fraction of Bean Cotyledons," Plant Physiol., (1969) vol. 44 pp. 1217-1226.

Qui, Yongge et al., "Progress in Mevalonate 5-Disphosate Decarboxylase and Its Inhibition," Journal of Hanshan Normal University, Dec. 2007 vol. 28, No. 6, pp. 73-82.

GenBank Database, Accession No: YP_024134, Disphosphomevalonate Decarboxylase, Futterer O. et.al., Dec. 3, 2007.

Lou, Jian et. al. "Research and Development of 3-Hydroxypropionic Acid by Microbes and Engineered Cells," Industrial Microbiology, (2006) vol. 36, No. 4, pp. 56-60.

Meier, Ingrid K. et al., "Olefin Synthesis by Vanadium (V)-induced Oxidative Decarboxylation-Deoxygenation of 3-Hydroxy Carboxylic Acids," Journal of Organic Chemistry, (1990) vol. 55, pp. 5619-5642.

Thompson, J. E. and Spencer, M, "Preparation and properties of an Enzyme System for Ethylene Production" Nature, (1966) vol. 210:5036, pp. 595-597.

Shimokawa, K. et al., "The Role of Beta-Hydroxy Propionate in Ethylene Biosynthesis, part 2. Ethylene Formation from Propionate-2-Carbon-14 in Banana Pulp Slices and Homogenates", Agricultural and Biological Chemistry, (1970) vol. 34:11, pp. 1640-1645.

Database UniProt XP002579929 (Jul. 5, 2004).

Jabalquinto, A. M. et al., "Substrate Binding Order in Mevalonate 5-Diphosphate Decarboxylase from Chicken Liver", Biochimica et Biophysica Acta—Protein Structure and Molecular Enzymology (1989), vol. 996:3 pp. 257-259.

Toth, M. et al., "Molecular Cloning and Expression of the cDNAs Encoding Human and Yeast Mevalonate Pyrophosphate Decarboxylase", Journal of Biological Chemistry, (1996) vol. 271:14, pp. 7895-7898.

XP-002579930—Database PREV197764059311 (1977).

XP-002579931—Database PREV200000216573 (Apr. 2000).

Office Action dated Jan. 12, 2015 and received in U.S. Appl. No. 13/002,504.

Final Office Action dated Jun. 10, 2015 and received in U.S. Appl. No. 13/002,504.

Restriction Requirement dated Apr. 23, 2015 and received in U.S. Appl. No. 14/390,774.

Office Action dated Jul. 15, 2015 and received in U.S. Appl. No. 14/390,774.

\* cited by examiner

Reaction catalyzed by mevalonate diphosphate decarboxylase EC 4.1.1.33

3-hydroxybutyrate 3-hydroxy-3-methylbutyrate 3-hydroxyvalerate 3-hydroxy-3-methylvalerate Propanol diphosphate Ethanol diphosphate Methanol diphosphate Pyrophosphate

PRODUCTION OF ALKENES BY COMBINED ENZYMATIC CONVERSION OF 3-HYDROXYALKANOIC ACIDS This Application is the National Phase under 35 U.S.C. §371 of PCT International Application No. PCT/EP2011/068174 which has an international filing date of Oct. 18, 2011, which claims priority to European Patent Application EP10188001 filed on Oct. 19, 2010. The entire contents of these applications listed above are hereby incorporated by reference.

The present invention relates to a method for generating alkenes through a biological process. More specifically, the invention relates to a method for producing alkenes (for example propylene, ethylene, 1-butylene, isobutylene or isoamylene) from molecules of the 3-hydroxyalkanoate type.

A large number of chemical compounds are currently derived from petrochemicals. Alkenes (such as ethylene, propylene, the different butenes, or else the pentenes, for example) are used in the plastics industry, for example for producing polypropylene or polyethylene, and in other areas of the chemical industry and that of fuels.

Ethylene, the simplest alkene, lies at the heart of industrial organic chemistry: it is the most widely produced organic compound in the world. It is used in particular to produce polyethylene, a major plastic. Ethylene can also be converted to many industrially useful products by reaction (of oxidation, of halogenation).

Propylene holds a similarly important role: its polymerization results in a plastic material, polypropylene. The technical properties of this product in terms of resistance, density, solidity, deformability, and transparency are unequalled. The worldwide production of polypropylene has grown continuously since its invention in 1954.

Butylene exists in four forms, one of which, isobutylene, enters into the composition of methyl-tert-butyl-ether (MTBE), an anti-knock additive for automobile fuel. Isobutylene can also be used to produce isooctene, which in turn can be reduced to isooctane (2,2,4-trimethylpentane); the very high octane rating of isooctane makes it the best fuel for so-called "gasoline" engines.

Amylene, hexene and heptene exist in many forms according to the position and configuration of the double bond. These products have real industrial applications but are less important than ethylene, propylene or butenes.

All these alkenes are currently produced by catalytic cracking of petroleum products (or by a derivative of the Fisher-Tropsch process in the case of hexene, from coal or gas). Their cost is therefore naturally indexed to the price of oil. Moreover, catalytic cracking is sometimes associated with considerable technical difficulties which increase process complexity and production costs.

Independently of the above considerations, the bioproduction of plastics ("bioplastics") is a thriving field. This boom is driven by economic concerns linked to the price of oil, and by environmental considerations that are both global (carbon-neutral products) and local (waste management).

The main family of bioplastics is that of the polyhydroxyalkanoates (PHA). These are polymers obtained by condensation of molecules comprising both an acid group and an alcohol group. Condensation takes place by esterification of the acid on the alcohol of the following monomer. This ester bond is not as stable as the direct carbon-carbon bond present in the polymers of conventional plastics, which explains why PHAs have a biodegradability of a few weeks to a few months.

The PHA family includes in particular poly-3-hydroxybutyrate (PHB), a polymer of 3-hydroxybutyrate, and polyhydroxybutyrate-valerate (PHBV), an alternating polymer of 3-hydroxybutyrate and 3-hydroxyvalerate.

PHB is naturally produced by some strains of bacteria such as *Alcaligenes eutrophus* and *Bacillus megaterium*. Laboratory bacteria, like *E. coli*, having integrated synthetic pathways leading to PHB or to PHAs in general, have been constructed. The compound or its polymer can, in certain laboratory conditions, account for up to 80% of the bacterial mass (Wong M S et al., Biotech. Bioeng. 99 (2008), 919-928). Industrial-scale production of PHB was attempted in the 1980s, but the costs of producing the compound by fermentation were considered too high at the time. Projects involving the direct production of these compounds in genetically modified plants (having integrated the key enzymes of the PHB synthetic pathway present in producer bacteria) are in progress and might entail lower operating costs.

The biological production of alkanes or other hydrocarbon molecules that can be used as fuels or as precursors of synthetic resins is called for in the context of a sustainable industrial operation in harmony with geochemical cycles. The first generation of biofuels consisted in the fermentative production of ethanol, as fermentation and distillation processes already existed in the food processing industry. The production of second generation biofuels is in an exploratory phase, encompassing in particular the production of long chain alcohols (butanol and pentanol), terpenes, linear alkanes and fatty acids. Two recent reviews provide a general overview of research in this field: Ladygina N et al., Process Biochemistry, 2006, 41:1001; and Wackett L P, Current Opinions in Chemical Biology, 2008, 21:187.

In the alkene chemical family, isoprene (2-methyl-1,3-butadiene) is the terpene motif which, through polymerization, leads to rubber. Other terpenes might be developed, by chemical, biological or mixed pathways, as usable products such as biofuels or to manufacture plastics. The recent literature shows that the mevalonate pathway (a key intermediate in steroid biosynthesis in many organisms) might be used in order to efficiently produce products from the terpene family at industrial yields (Withers S T et al., Appl. Environ. Microbiol., 2007, 73:6277).

The production of alkenes, in particular terminal alkenes, [ethylene mono- or di-substituted at position 2: $H_2C=C(R^1)(R^2)$] has apparently been less extensively investigated. The conversion of isovalerate to isobutylene by the yeast *Rhodotorula minuta* has been described (Fujii T. et al., Appl. Environ. Microbiol., 1988, 54:583), but the efficiency of this reaction, characterized by a very low value of the turnover number ($k_{cat}$ is $1\times10^{-5}$ sec$^{-1}$), is far from permitting an industrial application. The reaction mechanism was elucidated by Fukuda H et al. (BBRC, 1994, 201(2):516) and involves a cytochrome P450 enzyme which decarboxylates isovalerate by reduction of an oxoferryl group $Fe^v=O$. At no point does the reaction involve hydroxylation of isovalerate. Isovalerate is also an intermediate in leucine catabolism. Large-scale biosynthesis of isobutylene by this pathway seems highly unfavorable, since it would require the synthesis and degradation of one molecule of leucine to form one molecule of isobutylene. Also, the enzyme catalyzing the reaction uses heme as cofactor, poorly lending itself to recombinant expression in bacteria and to improvement of enzyme parameters. For all these reasons, it appears very unlikely that this pathway of the prior art can serve as a basis for industrial exploitation. Other microorganisms have been described as being marginally capable of naturally producing isobutylene from isovalerate; the yields obtained are even lower than those obtained with *Rhodotorula minuta* (Fukuda H. et al, Agric. Biol. Chem., 1984, 48:1679).

The same studies have also described the natural production of propylene: many microorganisms are capable of producing propylene, once again with an extremely low yield. The production of ethylene by plants has long been known (Meigh et al, 1960, Nature, 186:902). According to the metabolic pathway elucidated, methionine is the precursor of ethylene (Adams and Yang, PNAS, 1979, 76:170). Conversion of 2-oxoglutarate has also been described (Ladygina N et al., Process Biochemistry 2006, 41:1001). Since the production of a two-carbon molecule of ethylene consumes a four- or five-carbon molecule precursor, these pathways appear materially and energetically unfavorable for their industrial application.

Thus, there is a need for efficient methods for producing alkenes such as ethylene, propylene, 1-butylene, isobutylene, 1-amylene or isoamylene.

WO2010/001078 describes a process for producing alkenes by enzymatic conversion of 3-hydroxyalkanoic acids with an enzyme having the activity of a decarboxylase. Such a method is advantageous because it helps to avoid the use of petroleum products, to lower the costs of producing plastics and fuels and can have a considerable global environmental impact by allowing carbon to be stored in solid form. Although the method described in WO 2010/001078 allows to produce alkenes by enzymatically converting 3-hydroxyalkanoates, there is still a need for improvements, in particular as regards efficiency of the process so as to make it suitable for industrial purposes. The present application addresses this need.

The present invention describes a method for producing alkene compounds starting from a 3-hydroxyalkanoate through a biological process, in particular an enzymatic process, in which two types of enzymes are combined in order to increase the efficiency of the production rate. More specifically, the present invention relates to a method for producing an alkene, characterized in that it comprises the conversion of a 3-hydroxyalkanoate into said alkene by
(i) a first enzyme having an activity of converting the 3-hydroxyalkanoate into the corresponding 3-phosphonoxyalkanoate; and
(ii) a second enzyme being different from the first enzyme and having an activity of converting said 3-phosphonoxyalkanoate into said alkene.

The present invention also relates to the use of at least two enzymes, wherein one enzyme is selected from (i) as specified above and the other enzyme is selected from (ii) as specified above or of a microorganism producing said combination of enzymes, for producing an alkene compound from a 3-hydroxyalkanoate.

The present invention also relates to organisms, preferably microorganisms, which produce at least two enzymes, wherein one enzyme is selected from (i) as specified above and the other enzyme is selected from (ii) as specified above.

"3-hydroxyalkanoate", as used herein, denotes a molecule responding to the following general formula:

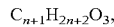

with 1<n<7, and comprising 3-hydroxypropionate as a common motif (FIG. 1), and optionally one or two alkyl substitutions on carbon 3. Said alkyl residues or groups can be linear or branched. As used herein, the terms "alkoyl" and "alkyl" have the same meaning and are interchangeable. Likewise, the terms "residue" and "group" have the same meaning and are interchangeable. Methyl, ethyl, propyl, isopropyl, butyl, isobutyl groups are examples of said alkyl groups. Carbon 3 becomes a chiral center if the two alkyl substitutions are different. The present definition encompasses the two chiral forms, even if one of the two forms, for example the R form, is the main form produced naturally. Examples of 3-hydroxyalkanoates are presented in FIG. 3. Optionally, alkyl substituents can be added on carbon 2, which then may also become chiral (if the two substituents are different). Equally, the configurations of the 3-hydroxyalkanoate substrates in the present invention encompass all the stereoisomers. In a preferred embodiment, the 3-hydroxyalkanoates correspond either to 3-hydroxypropionate or to variants or derivatives of 3-hydroxypropionate in which one of the two or the two hydrogen atoms carried on carbon 3 are substituted by a motif composed solely of carbon and hydrogen atoms, the number of carbon atoms of said substituents ranging from 1 to 5, preferably from 1 to 3, such as methyl, ethyl, propyl, isopropyl, butyl or isobutyl. The suffix "oate", as used herein, can interchangeably denote either the carboxylate ion (COO—) or carboxylic acid (COOH). It is not used to denote an ester. In a particular embodiment, the 3-hydroxyalkanoates are represented by the following formula: HO—CO—CH$_2$—C(R$^1$)(R$^2$)—OH or O$^-$—CO—CH$_2$—C(R$^1$)(R$^2$)—OH.

The term "3-phosphonoxyalkanoate" denotes a molecule which responds to the following general formula:

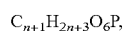

with 1<n<7, and comprising 3-phosphonoxypropionate as a common motif, and optionally one or two alkyl substitutions on carbon 3.

The term "alkene", as used herein, denotes molecules composed solely of carbon and hydrogen, containing one carbon-carbon double bond and having the chemical formula of a mono-unsaturated hydrocarbon, $C_nH_{2n}$, where n equals at least two. Preferably, n equals at least 3, 4, 5 or 6. Most preferably n is at most 6. Thus, generally, the term "alkene" refers to a molecule responding to the formula $C_nH_{2n}$, with 1<n<7.

In a preferred embodiment alkenes are represented by the structural formula H$_2$C=C(R$^1$)(R$^2$) wherein R$^1$ and R$^2$ are selected, independently, from the group consisting of a hydrogen atom and a linear or branched alkyl radical, so that the total number of carbon atoms in the alkene molecule is at most 6.

Preferred examples of alkene compounds according to the invention are in particular ethylene, propylene, isobutylene, and isoamylene (FIG. 4), or else 1-butylene and 1-amylene.

"Carbon source", as used herein, denotes any carbon compound that can be used as substrate for the organisms according to the invention. Said term includes glucose or any other hexose, xylose or any other pentose, polyols such as glycerol, sorbitol or mannitol, or else polymers such as starch, cellulose or hemicellulose, or else poly-3-hydroxyalkanoates like poly-3-hydroxybutyrate. It may be any substrate allowing the growth of microorganisms, such as formate for example. It may also be CO$_2$ in the case where the organisms are capable of carrying out photosynthesis.

"Recombinant", as used herein, denotes the artificial genetic modification of an organism, either by addition, removal, or modification of a chromosomal or extra-chromosomal gene or regulatory motif such as a promoter, or by fusion of organisms, or by addition of a vector of any type, for example plasmidic. The term "recombinant expression" denotes the production of a protein involving a genetic modification, preferably in order to produce a protein of exogenous or heterologous origin with respect to its host, that is, which does not naturally occur in the production host, or in order to produce a modified or mutated endogenous protein.

"Overexpression" or "overexpressing", as used herein, denotes the recombinant expression of a protein in a host organism, preferably originating from an organism different from the one in which it is expressed, increased by at least 10% and preferably by 20%, 50%, 100%, 500% and possibly more as compared to the natural expression of said protein occurring in said host organism. This definition also encompasses the case where there is no natural expression of said protein.

A "co-substrate" is a compound or molecule added to the enzymatic reaction, so as to improve certain parameters thereof, and above all the activity thereof, said product and the principal substrate being consumed in equal amounts. The co-substrate must therefore be added to the reaction at a concentration comparable to that of the principal substrate. Depending on the enzyme, the presence of a co-substrate may be required for the enzymatic reaction.

A "cofactor" is a product added to the enzymatic reaction, so as to improve certain parameters thereof and above all to improve the activity thereof, said product not being consumed during the reaction, and therefore needing only to be added at a low concentration, proportional to the amount of enzyme, said concentration therefore being referred to as "catalytic".

A "part" of an amino acid sequence denotes a fragment comprising at least 10, preferably at least 20, 30, 40 or 50 consecutive amino acid residues of said sequence.

"Homology", as used herein, denotes the existence of a similarity between two sequences as measured by the percent identity between said two sequences. In a preferred embodiment the term "homology" means sequence identity.

Chemical compounds are often known by several names, official or common. Herein, the common names of the molecules are preferred. Thus:
 "ethylene" is used to denote ethene
 "propylene" is used to denote propene
 "butylene" is used to denote butene
 "isobutylene" is used to denote 2-methylpropene or isobutene
 "amylene" is used to denote pentene
 "isoamylene" is used to denote 2-methyl-but-1-ene or isopentene
 "propionate" is used to denote propanoic acid or the propanoate ion
 "butyrate" is used to denote butanoic acid or the butanoate ion
 "valerate" is used to denote pentanoic acid or the pentanoate ion.

The present invention describes a method for producing alkene compounds starting from a 3-hydroxyalkanoate through a biological process, in particular an enzymatic process, in which two types of enzymes are combined in order to increase the efficiency of the production rate. More specifically, the present invention relates to a method for producing an alkene, characterized in that it comprises the conversion of a 3-hydroxyalkanoate into said alkene by
(i) a first enzyme having an activity of converting the 3-hydroxyalkanoate into the corresponding 3-phosphonoxyalkanoate; and
(ii) a second enzyme being different from the first enzyme and having an activity of converting said 3-phosphonoxyalkanoate into said alkene.

As mentioned above, WO 2010/001078 describes a process for producing alkenes by enzymatic conversion of 3-hydroxyalkanoic acids with an enzyme having the activity of a decarboxylase. It has been described in WO 2010/001078 that generally the conversion of a 3-hydroxyalkanoate into an alkene by an enzyme having a decarboxylase activity, e.g. a mevalonate diphosphate (MDP) decarboxylase (E.C. 4.1.1.33) takes place by the conversion of the 3-hydroxyalkanoate into the corresponding 3-phosphonoxyalkanoate which is then decarboxylated to lead to the corresponding alkene. The generic reaction carried out by MDP decarboxylase using various 3-hydroxyalkanoates is depicted in FIG. 2B.

It has now been found that different decarboxylases, in particular mevalonate diphosphate decarboxylases, catalyze the two above mentioned steps with different efficiencies, i.e. that some decarboxylases catalyze the first step with a higher efficiency than other decarboxylases and that some decarboxylases show a preference for the second step, i.e. the decarboxylation step, and that therefore the efficiency of the conversion of the 3-hydroxyalkanoate into the alkene as described in WO 2010/001078 can be significantly increased by combining corresponding enzymes. Thus, the present invention in particular relates to a method for achieving a higher efficiency in the enzymatic production of alkenes from 3-hydroxyalkanoates, i.e. a method for improving the efficiency of such an enzymatic production.

The term "an enzyme having an activity of converting the 3-hydroxyalkanoate into the corresponding 3-phosphonoxyalkanoate" means an enzyme which can phosphorylate a 3-hydroxyalkanoate into the corresponding 3-phosphonoxyalkanoate. The phosphate group comes preferably from an ATP molecule.

This activity can, e.g., be measured as described in the attached Examples, in particular Example 5. One possibility is thus to incubate the respective enzyme with the 3-hydroxyalkanoate and ATP and to measure the production of ADP (which reflects the production of the corresponding 3-phosphonoxyalkanoate). Assays for measuring the production of ADP are known to the person skilled in the art. One of these methods is the pyruvate kinase/lactate dehydrogenase assay described in Example 5. In this case the assay measures the rate of NADH absorbance decrease at 340 nm which is proportional to the ADP quantity. In a preferred embodiment the term "an enzyme having an activity of converting the 3-hydroxyalkanoate into the corresponding 3-phosphonoxyalkanoate" means an enzyme which can convert 3-hydroxyisovalerate and ATP into 3-phosphonoxyisovalerate and ADP. Even more preferably such an enzyme can catalyze the reaction of converting the 3-hydroxyalkanoate into the corresponding 3-phosphonoxyalkanoate, preferably the reaction of converting 3-hydroxyisovalerate and ATP into 3-phosphonoxyisovalerate and ADP, with a $K_M$ of 10 mM or lower, e.g. with a $K_M$ of 5 mM or lower, preferably of 1 mM or lower and even more preferably of 0.1 mM or lower. In a particularly preferred embodiment such an enzyme can catalyze the reaction of converting the 3-hydroxyalkanoate into the corresponding 3-phosphonoxyalkanoate, preferably the reaction of converting 3-hydroxyisovalerate and ATP into 3-phosphonoxyisovalerate and ADP, with a $k_{cat}$ of at least 0.2 s$^{-1}$, preferably with a $k_{cat}$ of at least 0.5 s$^{-1}$, particularly preferred with a $k_{cat}$ of at least 1.0 s$^{-1}$, more preferred of at least 2.0 s$^{-1}$ and even more preferred with a $k_{cat}$ of at least 5.0 s$^{-1}$.

In a particularly preferred embodiment the capacity to convert 3-hydroxyisovalerate and ATP into 3-phosphonoxyisovalerate and ADP is measured in an assay as described in Example 5.

The term "an enzyme having an activity of converting said 3-phosphonoxyalkanoate into said alkene" means an enzyme which can catalyze a reaction by which there is a decarboxylation and dephosphorylation of the 3-phosphonoxyalkanoate thereby leading to the corresponding alkene.

This activity can, e.g., be measured as described in the appended Examples, in particular in Example 8. One possibility is thus to incubate the respective enzyme with the corresponding phosphonoxyalkanoate under conditions which in principle allow the decarboxylation and the dephosphorylation and to detect the production of the corresponding alkene, e.g. by gas chromatography. In a preferred embodiment the term "an enzyme having an activity of converting said 3-phosphonoxyalkanoate into said alkene" means an enzyme which can convert 3-phosphonoxyisovalerate into isobutene, preferably under the conditions described in Example 8. Even more preferably such an enzyme can catalyze the reaction of converting the 3-phosphonoxyalkanoate into the corresponding alkene (via decarboxylation and dephosphorylation) with a $K_M$ of 100 mM or lower, e.g. with a $K_M$ of 75 mM or lower, or with a $K_M$ of 50 mM or lower, preferably of 10 mM or lower or 5 mM or lower or 1 mM or lower, and even more preferably of 0.1 mM or lower. In a particularly preferred embodiment such an enzyme can catalyze the reaction of converting the 3-phosphonoxyalkanoate into the corresponding alkene, preferably the reaction of converting 3-phosphonoxyisovalerate into isobutene, with a $k_{cat}$ of at least $10^{-6}$ s$^{-1}$, preferably with a $k_{cat}$ of at least $10^{-4}$ s$^{-1}$, e.g. with a $k_{cat}$ of at least $10^{-3}$ s$^{-1}$ or with a $k_{cat}$ of at least $10^{-2}$ s$^{-1}$, such as with a $k_{cat}$ of at least $10^{-1}$ s$^{-1}$, for example with a $k_{cat}$ of at least 0.2 s$^{-1}$, preferably with a $k_{cat}$ of at least 0.5 s$^{-1}$, particularly preferred with a $k_{cat}$ of at least 1.0 s$^{-1}$, more preferred of at least 2.0 s$^{-1}$ and even more preferred with a $k_{cat}$ of at least 5.0 s$^{-1}$.

In a particularly preferred embodiment the capacity to convert 3-phosphonoxyisovalerate into isobutene is measured in an assay as described in Example 8.

In one preferred embodiment an enzyme mentioned in (i) and (ii), above, is an enzyme which is considered by NCBI or an equivalent engine as having a COG3407 domain.

In a preferred embodiment of the method according to the invention the first enzyme
(i) having an activity of converting the 3-hydroxyalkanoate into the corresponding 3-phosphonoxyalkanoate is selected from the group consisting of
(A) a protein comprising the amino acid sequence as shown in SEQ ID NO: 1 or a protein comprising an amino acid sequence which is at least 15% identical to the amino acid sequence shown in SEQ ID NO: 1 and showing an activity of converting the 3-hydroxyalkanoate into the corresponding 3-phosphonoxyalkanoate which is at least as high as the corresponding activity of the protein having the amino acid sequence shown in SEQ ID NO: 1;
(B) a protein comprising the amino acid sequence as shown in SEQ ID NO: 2 or a protein comprising an amino acid sequence which is at least 15% identical to the amino acid sequence shown in SEQ ID NO: 2 and showing an activity of converting the 3-hydroxyalkanoate into the corresponding 3-phosphonoxyalkanoate which is at least as high as the corresponding activity of the protein having the amino acid sequence shown in SEQ ID NO: 2;
(C) a protein comprising the amino acid sequence as shown in SEQ ID NO: 3 or a protein comprising an amino acid sequence which is at least 15% identical to the amino acid sequence shown in SEQ ID NO: 3 and showing an activity of converting the 3-hydroxyalkanoate into the corresponding 3-phosphonoxyalkanoate which is at least as high as the corresponding activity of the protein having the amino acid sequence shown in SEQ ID NO: 3; and
(D) a protein comprising the amino acid sequence as shown in SEQ ID NO: 4 or a protein comprising an amino acid sequence which is at least 15% identical to the amino acid sequence shown in SEQ ID NO: 4 and showing an activity of converting the 3-hydroxyalkanoate into the corresponding 3-phosphonoxyalkanoate which is at least as high as the corresponding activity of the protein having the amino acid sequence shown in SEQ ID NO: 4.

SEQ ID NO: 1 shows the amino acid sequence of an enzyme from *Picrophilus torridus* DSM 9790 (GenBank accession number AAT43941; Swissprot/TrEMBL accession number Q6KZB1).

SEQ ID NO: 2 shows the amino acid sequence of an enzyme from *Thermoplasma acidophilum* (GenBank accession number CAC12426; Swissprot/TrEMBL accession number Q9HIN1).

SEQ ID NO: 3 shows the amino acid sequence of an enzyme from *Thermoplasma volcanium* (GenBank accession number BAB59465; Swissprot/TrEMBL accession number Q97BY2).

SEQ ID NO: 4 shows the amino acid sequence of an enzyme from *Ferroplasma acidarmanus* fer1 (GenBank accession number ZP_05571615).

In a further preferred embodiment of the method according to the invention the second enzyme (ii) having an activity of converting said 3-phosphonoxyalkanoate into said alkene is selected from the group consisting of
(a) a protein comprising the amino acid sequence as shown in SEQ ID NO: 5 or a protein comprising an amino acid sequence which is at least 15% identical to the amino acid sequence shown in SEQ ID NO: 5 and showing an activity of converting said 3-phosphonoxyalkanoate into said alkene which is at least as high as the corresponding activity of the protein having the amino acid sequence shown in SEQ ID NO: 5;
(b) a protein comprising the amino acid sequence as shown in SEQ ID NO: 6 or a protein comprising an amino acid sequence which is at least 15% identical to the amino acid sequence shown in SEQ ID NO: 6 and showing an activity of converting said 3-phosphonoxyalkanoate into said alkene which is at least as high as the corresponding activity of the protein having the amino acid sequence shown in SEQ ID NO: 6;
(c) a protein comprising the amino acid sequence as shown in SEQ ID NO: 7 or a protein comprising an amino acid sequence which is at least 15% identical to the amino acid sequence shown in SEQ ID NO: 7 and showing an activity of converting said 3-phosphonoxyalkanoate into said alkene which is at least as high as the corresponding activity of the protein having the amino acid sequence shown in SEQ ID NO: 7;
(d) a protein comprising the amino acid sequence as shown in SEQ ID NO: 8 or a protein comprising an amino acid sequence which is at least 15% identical to the amino acid sequence shown in SEQ ID NO: 8 and showing an activity of converting said 3-phosphonoxyalkanoate into said alkene which is at least as high as the corresponding activity of the protein having the amino acid sequence shown in SEQ ID NO: 8;
(e) a protein comprising the amino acid sequence as shown in SEQ ID NO: 9 or a protein comprising an amino acid sequence which is at least 15% identical to the amino acid sequence shown in SEQ ID NO: 9 and showing an activity of converting said 3-phosphonoxyalkanoate into said alkene which is at least as high as the corresponding activity of the protein having the amino acid sequence shown in SEQ ID NO: 9;

(f) a protein comprising the amino acid sequence as shown in SEQ ID NO: 10 or a protein comprising an amino acid sequence which is at least 15% identical to the amino acid sequence shown in SEQ ID NO: 10 and showing an activity of converting said 3-phosphonoxyalkanoate into said alkene which is at least as high as the corresponding activity of the protein having the amino acid sequence shown in SEQ ID NO: 10;

(g) a protein comprising the amino acid sequence as shown in SEQ ID NO: 11 or a protein comprising an amino acid sequence which is at least 15% identical to the amino acid sequence shown in SEQ ID NO: 11 and showing an activity of converting said 3-phosphonoxyalkanoate into said alkene which is at least as high as the corresponding activity of the protein having the amino acid sequence shown in SEQ ID NO: 11;

(h) a protein comprising the amino acid sequence as shown in SEQ ID NO: 12 or a protein comprising an amino acid sequence which is at least 15% identical to the amino acid sequence shown in SEQ ID NO: 12 and showing an activity of converting said 3-phosphonoxyalkanoate into said alkene which is at least as high as the corresponding activity of the protein having the amino acid sequence shown in SEQ ID NO: 12;

(i) a protein comprising the amino acid sequence as shown in SEQ ID NO: 13 or a protein comprising an amino acid sequence which is at least 15% identical to the amino acid sequence shown in SEQ ID NO: 13 and showing an activity of converting said 3-phosphonoxyalkanoate into said alkene which is at least as high as the corresponding activity of the protein having the amino acid sequence shown in SEQ ID NO: 13;

(j) a protein comprising the amino acid sequence as shown in SEQ ID NO: 14 or a protein comprising an amino acid sequence which is at least 15% identical to the amino acid sequence shown in SEQ ID NO: 14 and showing an activity of converting said 3-phosphonoxyalkanoate into said alkene which is at least as high as the corresponding activity of the protein having the amino acid sequence shown in SEQ ID NO: 14; and (k) a protein comprising the amino acid sequence as shown in SEQ ID NO: 15 or a protein comprising an amino acid sequence which is at least 15% identical to the amino acid sequence shown in SEQ ID NO: 15 and showing an activity of converting said 3-phosphonoxyalkanoate into said alkene which is at least as high as the corresponding activity of the protein having the amino acid sequence shown in SEQ ID NO: 15.

SEQ ID NO: 5 shows the amino acid sequence of an enzyme cloned from *Streptococcus gordonii*. SEQ ID NO: 6 shows the amino acid sequence of an enzyme from *Streptococcus gordonii* str. Challis substr. CH1 (GenBank accession number AAT43941; Swissprot/TrEMBL accession number A8UU9). SEQ ID NO: 7 shows the amino acid sequence of an enzyme from *Streptococcus infantarius* subsp *infantarius* ATCC BAA-102 (GenBank accession number EDT48420.1; Swissprot/TrEMBL accession number B1SCG0). SEQ ID NO: 8 shows the amino acid sequence of an enzyme from *Homo sapiens* (GenBank accession number AAC50440.1; Swissprot/TrEMBL accession number P53602.1). SEQ ID NO: 9 shows the amino acid sequence of an enzyme from *Lactobacillus delbrueckii* (GenBank accession number CAI9800.1; Swissprot/TrEMBL accession number Q1GAB2). SEQ ID NO: 10 shows the amino acid sequence of an enzyme from *Streptococcus mitis* (strain B6) (GenBank accession number CBJ22986.1). SEQ ID NO: 11 shows the amino acid sequence of an enzyme from *Streptococcus gallolyticus* UCN34 (GenBank accession number CBI13757.1). SEQ ID NO: 12 shows the amino acid sequence of an enzyme from *Streptococcus sanguinis* SK36 (GenBank accession number ABN43791.1). SEQ ID NO: 13 shows the amino acid sequence of an enzyme from *Streptococcus* sp. M143 (GenBank accession number EFA24040.1). SEQ ID NO: 14 shows the amino acid sequence of an enzyme from *Streptococcus suis* 89/1591 (GenBank accession number EEF63672.1). SEQ ID NO: 15 shows the amino acid sequence of an enzyme from *Streptococcus salivarius* SK126 (GenBank accession number EEK09252).

In a preferred embodiment of the method according to the invention the first enzyme (i) is as defined in (A) above and the second enzyme (ii) is as defined in (a) or (b) mentioned above, even more preferably the second enzyme is as defined in (f), (g), (h), (i), (j) or (k) mentioned above. As illustrated in the examples, the combination of these enzymes is particularly efficient at producing alkene compounds according to the present invention.

In another preferred embodiment of the method according to the invention the second enzyme (ii) having an activity of converting said 3-phosphonoxyalkanoate into said alkene is selected from any one of the proteins listed in the following Table or from a protein comprising an amino acid sequence which is at least 15% identical to the amino acid sequence of such a protein and showing an activity of converting said 3-phosphonoxyalkanoate into said alkene which is at least as high as the corresponding activity of said protein.

TABLE 1

| Organism | Ref sequence GenBank |
|---|---|
| *Methanosarcina mazei* | AAM31457.1 |
| *Methanocaldococcus jannaschii* | AAB98390.1 |
| *Staphylococcus saprophyticus* | BAE19266.1 |
| *Streptococcus agalactiae* | EAO73731.1 |
| *Enterococcus faecalis* | AAO80711.1 |
| *Flavobacterium johnsoniae* | ABQ04421.1 |
| *Bdellovibrio bacteriovorus* | CAE79505.1 |
| *Chloroflexus aurantiacus* | A9WEU8.1 |
| *Legionella pneumophila* | CAH13175.1 |
| *Listeria monocytogenes* | EAL09343.1 |
| *Metallosphaera sedula* | ABP95731.1 |
| *Staphylococcus epidermidis* | AAO03959.1 |
| *Streptococcus thermophilus* | AAV60266.1 |
| *Bacillus coagulans* | EAY45229.1 |
| *Chloroflexus aggregans* | EAV09355.1 |
| *Lactobacillus brevis* | ABJ64001.1 |
| *Lactobacillus fermentum* | BAG27529.1 |
| *Lactobacillus plantarum* | CAD64155.1 |
| *Lactobacillus salivarius* | ABD99494.1 |
| *Lactococcus lactis* sp. *lactis* | AAK04503.1 |
| *Dichelobacter nodosus* | ABQ14154.1 |
| *Flavobacterium psychrophilum* | CAL42423.1 |
| *Streptococcus pneumoniae* | EDT95457.1 |
| *Streptococcus pyogenes* | AAT86835.1 |
| *Streptococcus suis* | ABP91444.1 |
| *Staphylococcus haemolyticus* | BAE05710.1 |
| *Streptococcus equi* | ACG62435.1 |
| *Arabidopsis thaliana* | AAC67348.1 |
| *Borrelia afzelii* | ABH01961.1 |
| *Encephalitozoon cuniculi* | CAD25409.1 |
| *Streptomyces* sp. | BAB07791.1 |
| *Streptococcus agalactiae* | EAO73731.1 |
| *Streptococcus uberis* | CAR41735.1 |
| *Gallus gallus* | XP_423130 |
| *Salmo salmar* | ACI34234 |
| *Natromonas pharaonis* | CAI48881.1 |
| *Haloarcula marismortui* | AAV46412.1 |
| *Haloquadratum walsbyi* | CAJ51653.1 |

As mentioned above, not only the proteins having the specifically mentioned amino acid sequences listed in the respective SEQ ID NOs or in Table 1 can be used, but also proteins which are considered by NCBI or an equivalent engine as having a COG3407 domain and, more preferred, proteins the amino acid sequence of which shows a homology of at least 15% to the specifically mentioned amino acid sequence and which have a respective enzymatic activity at least as high as the activity of a protein having the specifically mentioned amino acid sequence. Preferred enzymes advantageously have at least x % homology, wherein x is selected from the group consisting of 20, 25, 20, 35, 40, 45, 50, 55 and 60. In a further preferred embodiment the enzyme has at least 65% sequence homology, preferably at least 70%, more preferably at least 75%, even more preferably, at least 80, 85, 90, 95, 96, 97, 98 or 99% homology to one of the sequences shown in SEQ ID NO: 1, 2, 3, 4, 5, 6, 7, 8, 9, 10, 11, 12, 13, 14 or 15 or to one of the sequences shown in Table 1. The percent of sequence homology can be determined by different methods and by means of software programs known to one of skill in the art, such as for example the CLUSTAL method or BLAST and derived software, or by using a sequence comparison algorithm such as that described by Needleman and Wunsch (J. Mol. Biol., 1970, 48:443) or Smith and Waterman (J. Mol. Biol., 1981, 147:195).

Such proteins showing the indicated degree of homology can, e.g., be other enzymes which occur naturally or which have been prepared synthetically. They include in particular enzymes which can be selected for their ability to produce alkenes according to the invention. Thus, a selection test comprises contacting the purified enzyme, or a microorganism producing the enzyme, with the substrate of the reaction and measuring the production of the respective compound, i.e. the 3-phosphonoxyalkanoate or the alkene. Such tests are described in the experimental section. Such selection tests can also be used to screen for enzymes with an optimized enzymatic activity for the substrate to be converted into the 3-phosphonoxyalkanoate or the alkene, i.e. having an optimized activity with respect to one or more 3-hydroxyalkanoates or 3-phosphonoxyalkanoates.

Such screening methods are well-known in the art and include, e.g. protein engineering techniques such as random mutagenesis, massive mutagenesis, site-directed mutagenesis, DNA shuffling, synthetic shuffling, in vivo evolution, or complete synthesis of genes and subsequent screening for the desired enzymatic activity.

The enzyme used in the invention can thus be natural or synthetic, and produced by chemical, biological or genetic means. It can also be chemically modified, for example in order to improve its activity, resistance, specificity, purification, or to immobilize it on a support.

Figure 2:
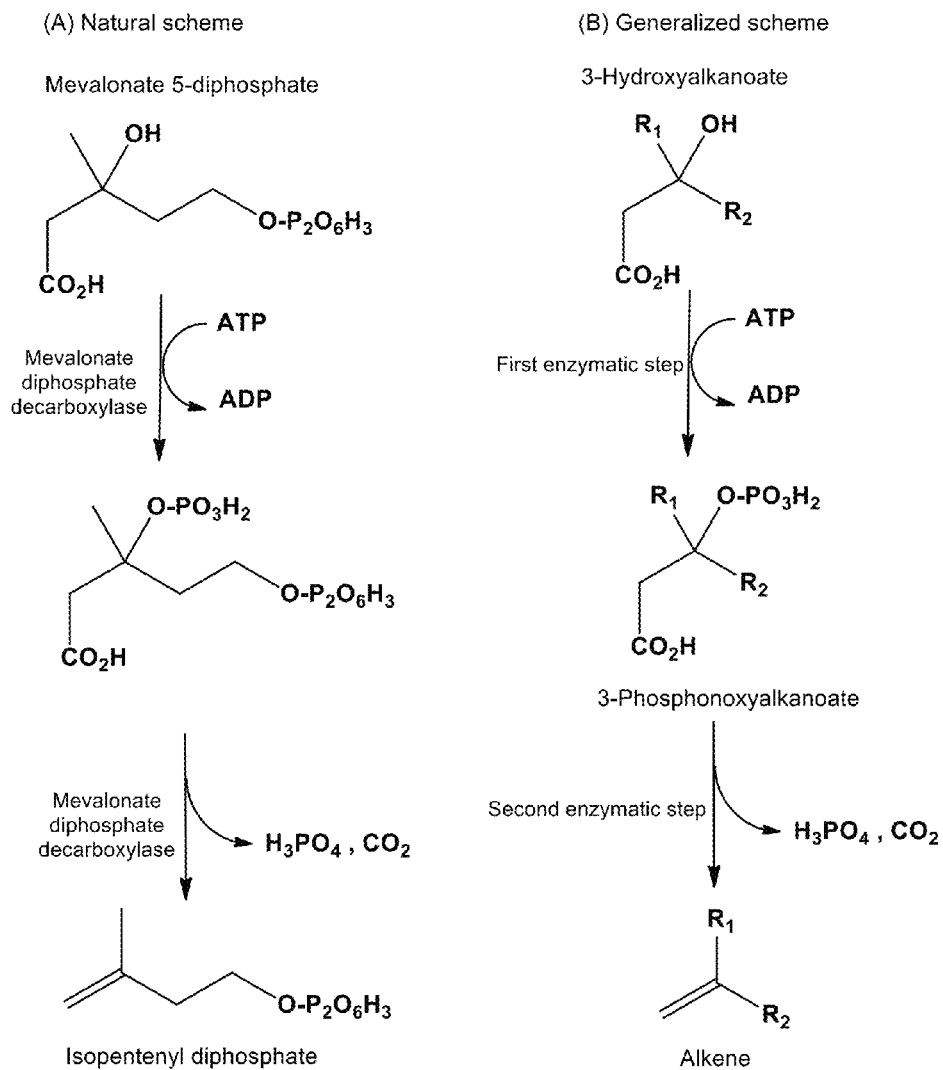

It has been found that enzymes which are able to catalyze the above described reactions for converting a 3-hydroxyalkanoate into an alkene via a 3-phospho-hydroxyalkanoate are often enzymes which can be classified in the phylogenetic superfamily of mevalonate diphosphate (MDP) decarboxylases (enzyme nomenclature EC 4.1.1.33). MDP decarboxylase is an enzyme involved in cholesterol biosynthesis. Said enzyme has been isolated from a variety of organisms including animals, fungi, yeasts and some bacteria. It can also be expressed by some plants (Lalitha et al., Phytochemistry 24 (11), (1985), 2569-2571). Many genes encoding this enzyme have been cloned and sequenced. These enzymes are generally composed of 300 to 400 amino acids and use ATP as co-substrate, which is converted during the reaction to ADP and inorganic phosphate. The phosphate group is transferred from the ATP molecule to the tertiary alcohol of mevalonate diphosphate, releasing ADP. The reaction intermediate phosphorylated on the 3-hydroxyl group then undergoes elimination of the phosphate group, in the physiological case releasing isopentenyl diphosphate (FIG. 2).

Accordingly, in a preferred embodiment, the enzyme defined in (i) or (ii) above, is a MDP decarboxylase. In the context of the present invention a MDP decarboxylase is defined as an enzyme which can at least catalyze the conversion of 5-diphospho-3-phosphomevalonate into isopentenyl-5-diphosphate and $CO_2$ or which can at least catalyze the reaction of converting mevalonate diphosphate and ATP into 5-diphospho-3-phosphomevalonate and ADP. Preferably, such an enzyme can catalyze both reactions.

In another preferred embodiment the enzyme defined in (i) above, is an enzyme as defined in (i) (B). The sequence shown in SEQ ID NO: 2 represents an enzyme identified in *Thermoplasma acidophilum*. In Genbank this enzyme is classified as a mevalonate diphosphate decarboxylase. However, it is known from Chen and Poulter (Biochemistry 49 (2010), 207-217) that in *Th. acidophilum* there exists an alternative mevalonate pathway which involves the action of a mevalonate-5-monophosphate decarboxylase. Thus, it is possible that the enzyme represented by SEQ ID NO: 2 actually represents a mevalonate-5-monophosphate decarboxylase. The same may hold true for other archae bacteria. Therefore, in another preferred embodiment the enzyme defined in (i) or (ii) above, is a mevalonate-5-monophosphate decarboxylase. Such an enzyme is capable of converting mevalonate-5-monophosphate into isopentenylpyrophosphate.

In preferred embodiments of the invention:
3-hydroxypropionate is converted via 3-phosphonoxypropionate into ethylene; or
3-hydroxybutyrate is converted via 3-phosphonoxybutyrate into propylene; or
3-hydroxyvalerate is converted via 3-phosphonoxyvalerate into 1-butylene; or
3-hydroxy-3-methylbutyrate (or 3-hydroxyisovalerate) is converted via 3-phosphonoxy-3-methylbutyrate (3-phosphonoxyisovalerate) into isobutylene; or
3-hydroxy-3-methylvalerate is converted via 3-phosphonoxy-3-methylvalerate into isoamylene.

The method according to the invention can be carried out in vitro, in the presence of isolated enzymes (or enzyme systems additionally comprising one or more cofactors). In vitro preferably means in a cell-free system.

In one embodiment, the enzymes employed in the method are used in purified form to convert 3-hydroxyalkanoates to alkenes. However, such a method may be costly, since enzyme and substrate production and purification costs are high.

Thus, in another preferred embodiment, the enzymes employed in the method are present in the reaction as a non-purified extract, or else in the form of non-lysed bacteria, so as to economize on protein purification costs. However, the costs associated with such a method may still be quite high due to the costs of producing and purifying the substrates.

Accordingly, in one preferred embodiment, the enzymes, native or recombinant, purified or not, are used to convert a 3-hydroxyalkanoate to an alkene. To do this, the enzymes are incubated in the presence of the substrate in physicochemical conditions allowing the enzymes to be active, and the incubation is allowed to proceed for a sufficient period of time. At the end of the incubation, one optionally measures the presence of the alkene by using any detection system known to one of skill in the art such as gas chromatography or colorimetric tests for measuring the formation of the alkene product, or of free phosphate, or else for measuring the disappearance of the 3-hydroxyalkanoate substrate or of ATP.

Figure 5:
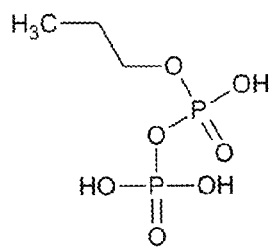
Figure 5:
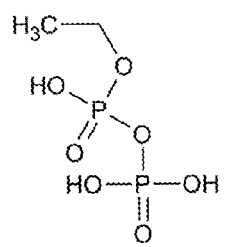
Figure 5:
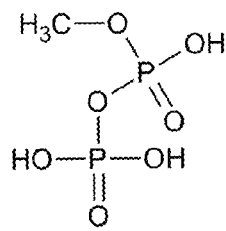
Figure 5:
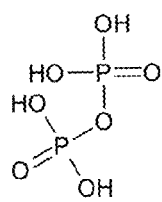

In a preferred embodiment, cofactors are added so as to best mimic the natural reaction or so as to provide steric or electronic complementation in the catalytic cleft. For example, if one of the enzymes used in the method according to the invention is an enzyme which naturally uses mevalonate disphosphate (MDP) as a substrate, the structure of 3-hydroxyalkanoates leaves a large space in the catalytic cleft empty during enzyme-substrate binding since generally a 3-hydroxyalkanoate corresponds to a fragment of MDP. Filling this space with a cofactor to replace the missing part of the substrate has the purpose of most closely mimicking the MDP molecule. As the cofactor is not modified during the reaction, it will therefore be added only in catalytic amounts. In the case where the substrate of the reaction is 3-hydroxypropionate, the complementary cofactor will be propyl diphosphate. In the case where the substrate is 3-hydroxybutyrate or 3-hydroxy-3-methyl butyrate, the complementary cofactor will be ethyl diphosphate. In the case where the substrate is 3-hydroxyvalerate or 3-hydroxy-3-methylvalerate, the complementary cofactor will be methyl diphosphate. These different molecules are shown in FIG. 5. By chance, it may happen that the complementary cofactor of a reaction has a positive effect on the reaction of another substrate. Generally, the cofactor can be any molecule comprising a phosphoanhydride, and therefore having the general global formula R—$PO_2H$—O—$PO_3H_2$, in which R is in particular H, a linear, branched or cyclic alkyl group, preferably having from 1 to 10 or from 1 to 5 carbon atoms, or any other monovalent organic group. The analogous motifs corresponding to methylene diphosphonate monoesters, having the general formula R—O—$PO_2H$—$CH_2$—$PO_3H_2$ in which phosphyanhydride is replaced by a methylene bridge having the advantage of not being hydrolyzed, are also part of the invention. More generally, the cofactors can be monophosphate, or even phosphate-free, analogs of the previous molecules, or else any other molecule that can improve the reaction yield by providing steric or electronic complementation in the enzyme catalytic site. The cofactor is advantageously selected from the group consisting of the pyrophosphate ion, methyl diphosphate, ethyl diphosphate, or propyl diphosphate.

In a preferred embodiment, the conversion occurs in the presence of a co-substrate, said co-substrate preferably being a compound containing a phosphoanhydride, and preferably being ATP, an rNTP, a dNTP or a mixture of several of these molecules, a polyphosphate, or pyrophosphate. The co-substrate is generally present in the host.

However, in another particular embodiment, a co-substrate can be added to the reaction, preferably selected from the group consisting of ATP, an rNTP, a dNTP, a mixture of several rNTPs or dNTPs, a polyphosphate, and preferably pyrophosphate, or a compound containing a phosphoanhydride (represented by the general formula X—$PO_3H_2$ of FIG. 2).

Although the decarboxylation step, i.e. the reaction defined as (ii) herein-above, does not require ATP consumption, it could be shown that the presence of ATP in the reaction could be beneficial. This has been demonstrated in Example 7, using 3-phosphonoxyisovalerate as a substrate. It is assumed that ATP might have an effect on the folding of the protein by the binding of ATP to the ATP-binding site of the diphosphomevalonate decarboxylase. In fact, this can be observed by eye: the purified enzyme has a tendency to precipitate, and the addition of ATP prevents this effect. It is considered that not only ATP but also other similar compounds like dATP, ADP, AMP or other NTPs or dNTPs have this effect. Thus, in a preferred embodiment, the method according to the present invention is carried with ATP, dATP, ADP, AMP or an NTP other than ATP or a dNTP as co-substrate.

In another preferred embodiment the method according to the invention is carried out in culture, in the presence of an organism, preferably a microorganism, producing the enzymes. Thus, in such an embodiment of the invention, an organism, preferably a microorganism, that produces the enzymes specified in (i) and (ii) above is used. In a preferred embodiment, the (micro)organism is recombinant in that the enzymes specified in (i) and (ii) produced by the host are heterologous relative to the production host. The method can thus be carried out directly in the culture medium, without the need to separate or purify the enzymes. In an especially advantageous manner, a (micro)organism is used having the natural or artificial property of endogenously producing one or more 3-hydroxyalkanoates, and also expressing or overexpressing the enzymes specified in (i) and (ii) above, natural or modified, so as to produce alkenes directly from a carbon source present in solution.

For example, the method according to the invention can be carried out by using microorganisms which produce one or more 3-hydroxyalkanoates [for example *Alcaligenes eutrophus* or *Bacillus megaterium*, or else an *E. coli* strain genetically modified so as to produce said product(s)] and which have been genetically engineered such that they overexpress the enzymes as defined in (i) and (ii) above, said enzymes preferably originating from an organism different from the host microorganism. The genetic modification can consist, e.g. in integrating the corresponding genes encoding the enzymes into the chromosome, expressing the enzymes from a plasmid containing a promoter upstream of the enzyme-coding sequence, the promoter and coding sequence preferably originating from different organisms, or any other method known to one of skill in the art. Alternatively, other bacteria or yeasts may have specific advantages and can be chosen. For instance, a yeast such as *Saccharomyces cerevisiae*, an extremophilic bacterium such as *Thermus thermophilus*, or anaerobic bacteria from the family Clostridiae, microalgae, or photosynthetic bacteria can be used.

The organisms used in the invention can be prokaryotes or eukaryotes, preferably, they are microorganisms such as bacteria, yeasts, fungi or molds, or plant cells or animal cells. In a particular embodiment, the microorganisms are bacteria, preferably of the genus *Escherichia*, *Alcaligenes* or *Bacillus* and even more preferably of the species *Escherichia coli*, *Alcaligenes eutrophus* or *Bacillus megaterium*.

In another preferred embodiment, the microorganisms are recombinant bacteria of the genus *Escherichia*, preferably of the species *Escherichia coli*, having been modified so as to endogenously produce one or more 3-hydroxyalkanoates, and converting them to alkenes.

In a further preferred embodiment the microorganism is a fungus, more preferably a fungus of the genus *Saccharomyces, Schizosaccharomyces, Aspergillus* or *Trichoderma* and even more preferably of the species *Saccharomyces cerevisiae, Schizosaccharomyces pombe, Aspergillus niger* or of the species *Trichoderma reesei*. In a particularly preferred embodiment the microorganism is a recombinant yeast producing 3-hydroxyalkanoates and converting them to alkenes due to the expression of the enzymes specified in (i) and (ii) above.

In another preferred embodiment, the method according to the invention makes use of a photosynthetic microorganism expressing the enzymes as specified in (i) and (ii) above. Preferably, the microorganism is a photosynthetic bacterium, or a microalgae. Even more preferably such a microorganism has the natural or artificial property of endogenously producing one or more 3-hydroxyalkanoates. In this case the microorganism would be capable of producing alkenes directly from $CO_2$ present in solution.

It is also conceivable to use in the method according to the invention one microorganism that produces an enzyme as defined in (i) above and another microorganism which produces an enzyme as defined in (ii) above. Moreover, in a further embodiment at least one of the microorganisms is capable of producing one or more 3-hydroxyalkanoates or, in an alternative embodiment, a further microorganism is used in the method which is capable of producing one or more 3-hydroxyalkanoates.

In another preferred embodiment the method according to the invention makes use of a multicellular organism expressing the enzymes as defined in (i) and (ii) above. Examples for such organisms are plants or animals.

In a particular embodiment, the method involves culturing microorganisms in standard culture conditions (30-37° C. at 1 atm, in a fermenter allowing aerobic growth of the bacteria) or non-standard conditions (higher temperature to correspond to the culture conditions of thermophilic organisms, for example).

In a further preferred embodiment the method of the invention is carried out in microaerophilic conditions. This means that the quantity of injected air is limiting so as to minimize residual oxygen concentrations in the gaseous effluents containing the alkene hydrocarbons.

In another preferred embodiment the method according to the invention furthermore comprises the step of collecting gaseous alkenes degassing out of the reaction, i.e. recovering the products which degas, e.g., out of the culture. Thus in a preferred embodiment, the method is carried out in the presence of a system for collecting alkene under gaseous form during the reaction.

As a matter of fact, short alkenes, and particularly ethylene, propylene and butene isomers, adopt the gaseous state at room temperature and atmospheric pressure. The method according to the invention therefore does not require extraction of the product from the liquid culture medium, a step which is always very costly when performed at industrial scale. The evacuation and storage of the gaseous hydrocarbons and their possible subsequent physical separation and chemical conversion can be performed according to any method known to one of skill in the art.

In a particular embodiment, the method also comprises detecting the alkene (for example propylene, ethylene or isobutylene) which is present in the gaseous phase. The presence of the compound to be produced in an environment of air or another gas, even in small amounts, can be detected by using various techniques and in particular by using gas chromatography systems with infrared or flame ionization detection, or by coupling with mass spectrometry.

In a particular embodiment, the alkenes produced by a method according to the invention are condensed, then optionally reduced, by using techniques known to one of skill in the art, so as to produce longer chain alkenes, or longer chain alkanes. For example, isobutylene can be used to synthesize isooctane: the catalytic methods for successfully carrying out this reaction have already been fully described.

In another embodiment, the method according to the invention is characterized by the conversion of a carbon source such as glucose, to 3-hydroxyalkanoate, followed by the conversion of said 3-hydroxyalkanoate into the corresponding alkene. The different steps of said method are outlined in FIG. 6.

In a particular embodiment, the method is characterized by the conversion of polyhydroxyalkanoates into 3-hydroxyalkanoate by using an enzyme or a suitable physicochemical method, followed by the conversion of said 3-hydroxyalkanoate into said alkene. Optionally, the polyhydroxyalkanoate has been produced by a microorganism or a plant whose metabolic pathways have been modified to as to produce high yields of polyhydroxyalkanoate.

In another embodiment, the method according to the invention comprises the production of alkenes from atmospheric $CO_2$ or from $CO_2$ artificially added to the culture medium. In this case the method is implemented in an organism which is able to carry out photosynthesis, such as for example microalgae.

The present invention also relates to a method for producing an alkene comprising the step of enzymatically converting a 3-phosphonoxyalkanoate into the corresponding alkene by use of an enzyme which can catalyze the conversion via decarboxylation and dephosphorylation.

As regards the preferred enzyme to be used in such a method, the same applies as has been set forth above in connection with (ii) of the method according to the invention as described herein-above.

Moreover, also with respect to the other preferred embodiments described above for the method according to the invention, the same applies to the method for producing an alkene from a 3-phosphonoxyalkanoate.

The present invention also relates to organisms, preferably microorganisms, which produce at least two enzymes, wherein one enzyme is selected from (i) as specified above and the other enzyme is selected from (ii) as specified above. In a preferred embodiment such an organism is a recombinant organism in the sense that it is genetically modified due to the introduction of at least one nucleic acid molecule encoding at least one of the above mentioned enzymes. Preferably such a nucleic acid molecule is heterologous with regard to the organism which means that it does not naturally occur in said organism.

Thus, the present invention also relates to an organism, preferably a microorganism, comprising a nucleic acid molecule coding for an enzyme as defined in (i) above and comprising a nucleic acid molecule coding for an enzyme as defined in (ii) above. In a preferred embodiment at least one of the nucleic acid molecules is heterologous to the organism which means that it does not naturally occur in said organism. The microorganism is preferably a bacterium, a yeast or a fungus. In another preferred embodiment the organism is a plant or non-human animal. As regards other preferred embodiments, the same applies as has been set forth above in connection with the method according to the invention.

Moreover, the present invention also relates to a composition comprising a microorganism according to the present invention, a suitable culture medium and a 3-hydroxyalkanoate compound or a carbon source that can be converted by the microorganism to a 3-hydroxyalkanoate compound.

The present invention also relates to the use of a combination of at least two enzymes, wherein one enzyme is selected from the following (i) and the other enzyme is selected from the following (ii) or of an organism, preferably a microorganism, according to the invention or of a composition according to the invention, for producing alkene compounds from 3-hydroxyalkanoates, wherein (i) and (ii) are as follows:

(i) a first enzyme having an activity of converting the 3-hydroxyalkanoate into the corresponding 3-phosphonoxyalkanoate; and (ii) a second enzyme being different from the first enzyme and having an activity of converting said 3-phosphonoxyalkanoate into said alkene.

As regards the preferred embodiments of the different components recited, the same applies as has been set forth above in connection with the method according to the invention.

Other aspects and advantages of the invention will be described in the following examples, which are given for purposes of illustration and not by way of limitation.

FIGURES LEGENDS

FIG. 1: The 3-hydroxypropionate motif.

FIG. 2: Reaction catalyzed by mevalonate diphosphate decarboxylase.

Figure 3:
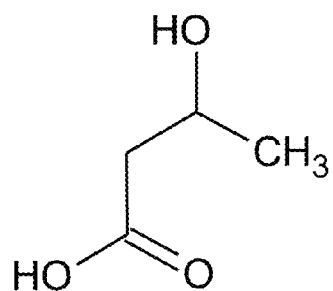
Figure 3:
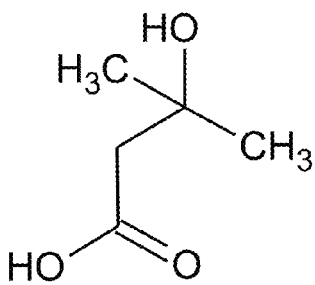
Figure 3:
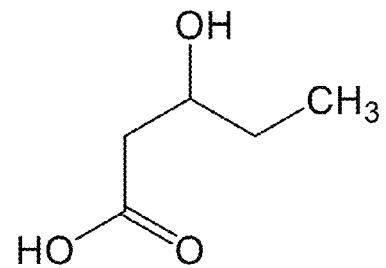
Figure 3:
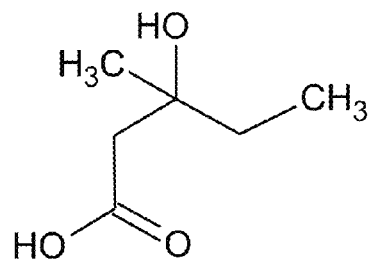

FIG. 3: Examples of 3-hydroxyalkanoates.

Figure 4:
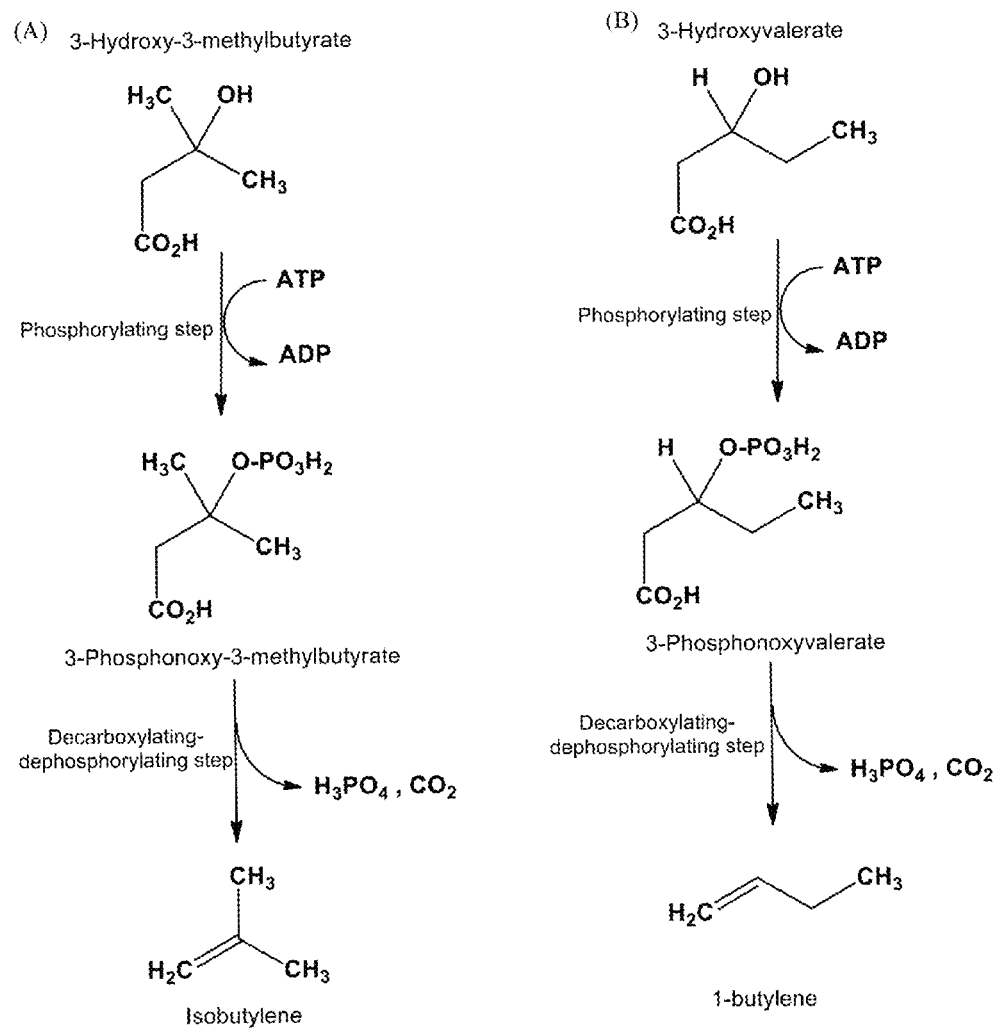
Figure 4:
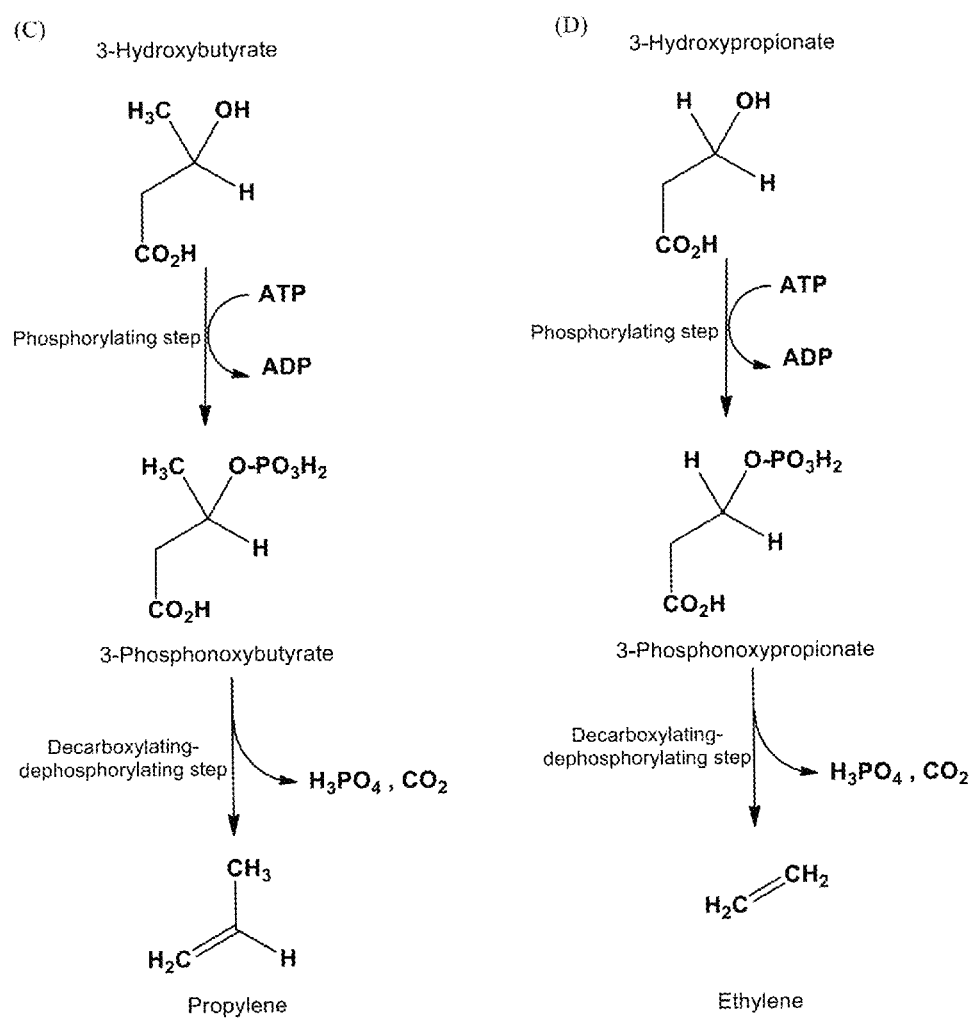
Figure 4:
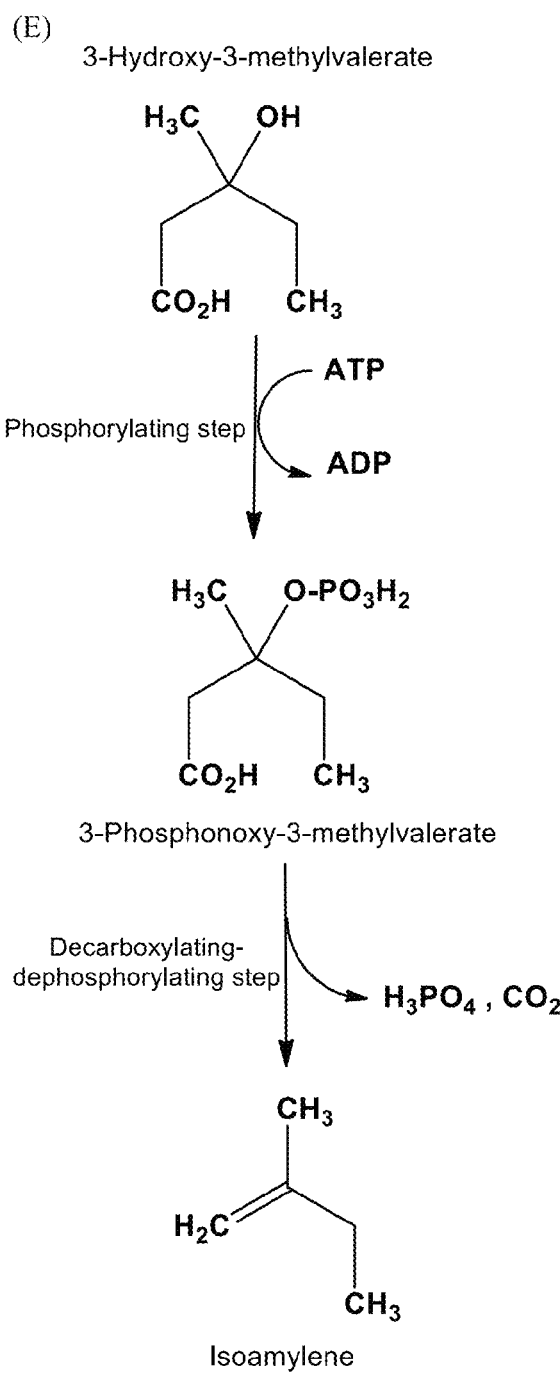

FIG. 4: Production of alkenes from 3-hydroxyalkanoates by combining two enzymatic steps.

FIG. 5: Cofactors that can be used in the reaction for the purpose of structural complementation in the catalytic site of mevalonate diphosphate decarboxylase.

Figure 6:
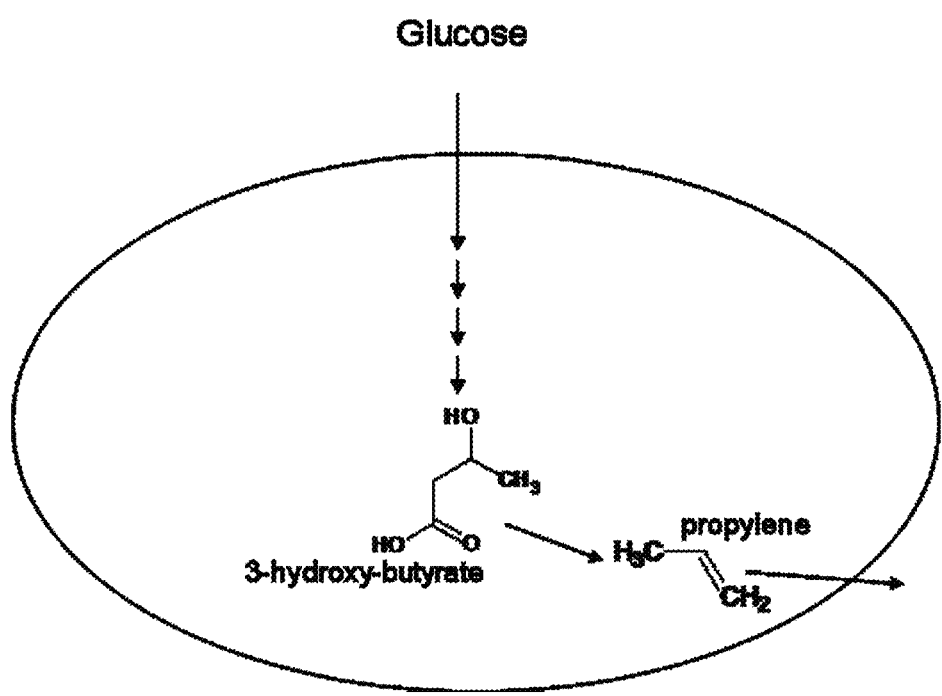

FIG. 6: Integrated method for producing an alkene from glucose.

Figure 7:
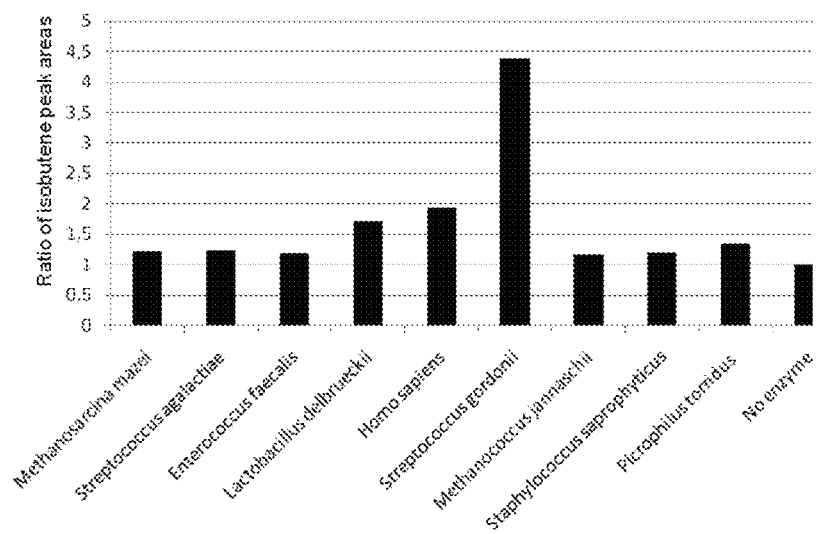

FIG. 7: Screening of MDP decarboxylases in a complementation assay. The reaction catalyzed by the *P. torridus* (SEQ ID NO:1) enzyme alone (0.1 mg) without a second enzyme, was taken as reference.

Figure 8:
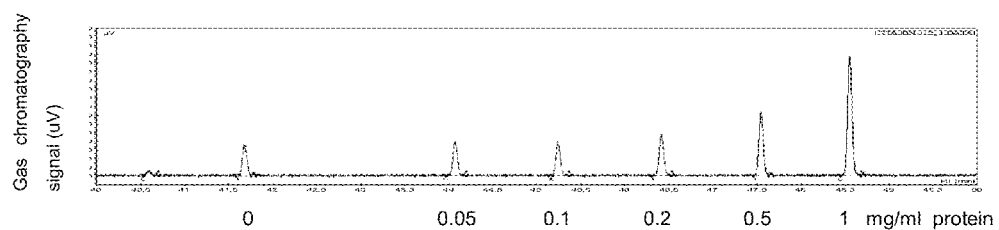

FIG. 8: Combined effect of MDP decarboxylase enzymes from *P. torridus* (SEQ ID NO:1) and *S. gordonii* (SEQ ID NO:5) for converting 3-hydroxyisovalerate (HIV) into isobutene (IBN). IBN production was measured as a function of the concentration of *S. gordonii* MDP decarboxylase (SEQ ID NO:5) added to a pre-incubated reaction mixture of HIV with 100 μg of *P. torridus* MDP decarboxylase (SEQ ID NO:1).

Figure 9:
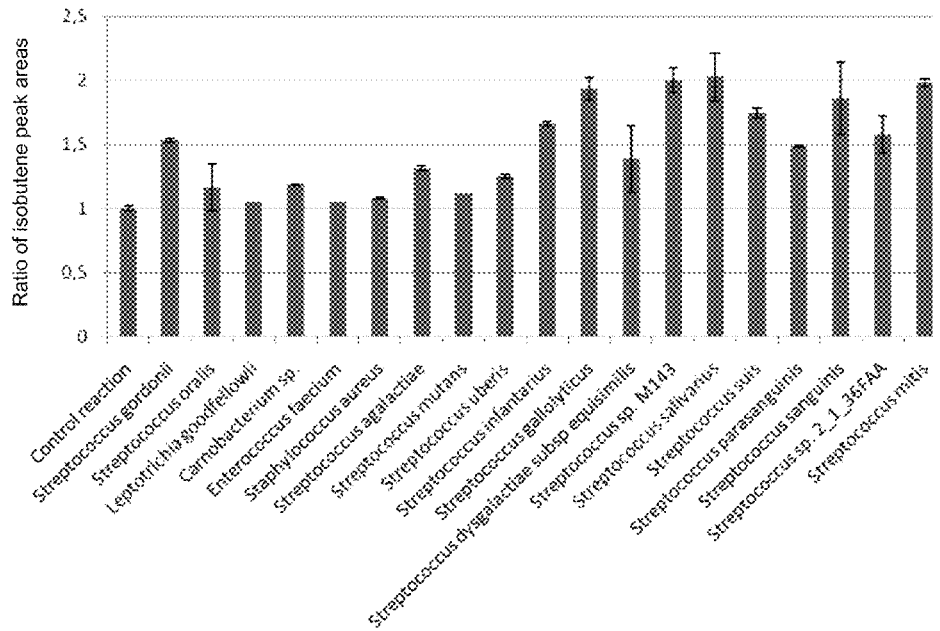

FIG. 9: Screening of enzyme homologs of *S. gordonii* MDP decarboxylase (SEQ ID NO:5). The peak area of isobutene obtained for the reaction with *Th. acidophilum* (SEQ ID NO:2) (0.1 mg) enzyme alone (no second enzyme), was used as reference (ratio=1).

MDP decarboxylases from the *Streptococcus* genus are particularly efficient when used in combination with an enzyme of the *P. torridus* phylum.

Figure 10:
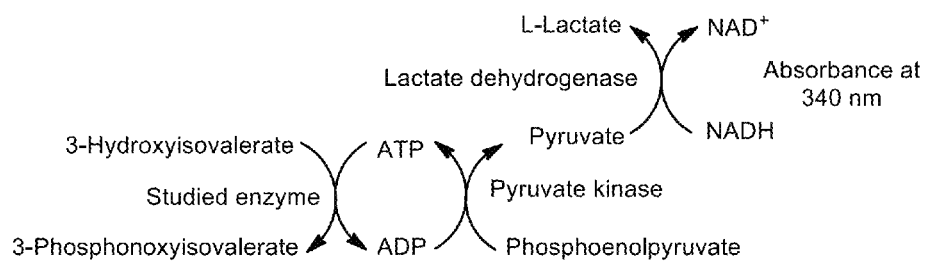

FIG. 10: Scheme of the ADP quantification assay, monitoring NADH consumption by the decrease of absorbance at 340 nm.

Figure 11:
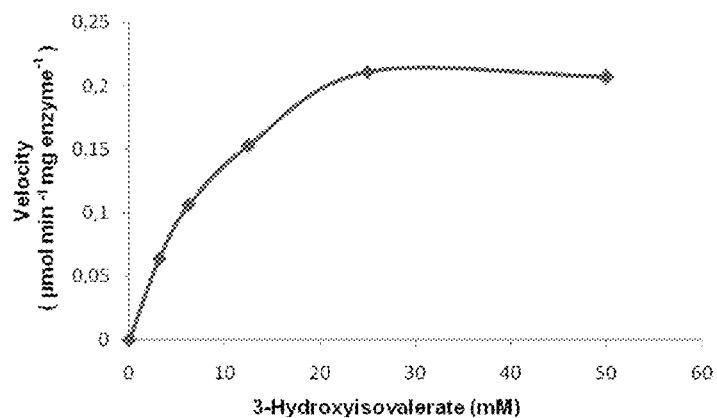

FIG. 11: Plot of the velocity as a function of substrate concentration for the phosphotransferase reaction catalyzed by *P. torridus* MDP decarboxylase (SEQ ID NO:1). Initial rates were computed from the kinetics over the 30 first minutes of the reaction.

Figure 12:
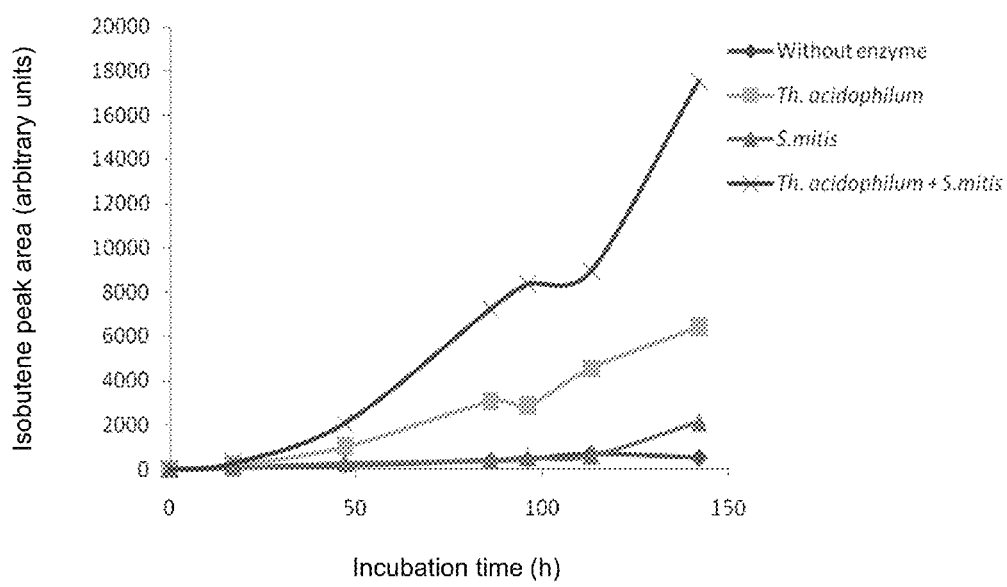

FIG. 12: Isobutene production from 3-hydroxyisovalerate in the following assays:

Without enzyme

In the presence of *S. mitis* MDP decarboxylase (SEQ ID NO:10)

In the presence of *Th. acidophilum* MDP decarboxylase (SEQ ID NO:2)

In the presence of both *Th. acidophilum* (SEQ ID NO:2) and *S. mitis* (SEQ ID NO:10) enzymes.

Figure 13:
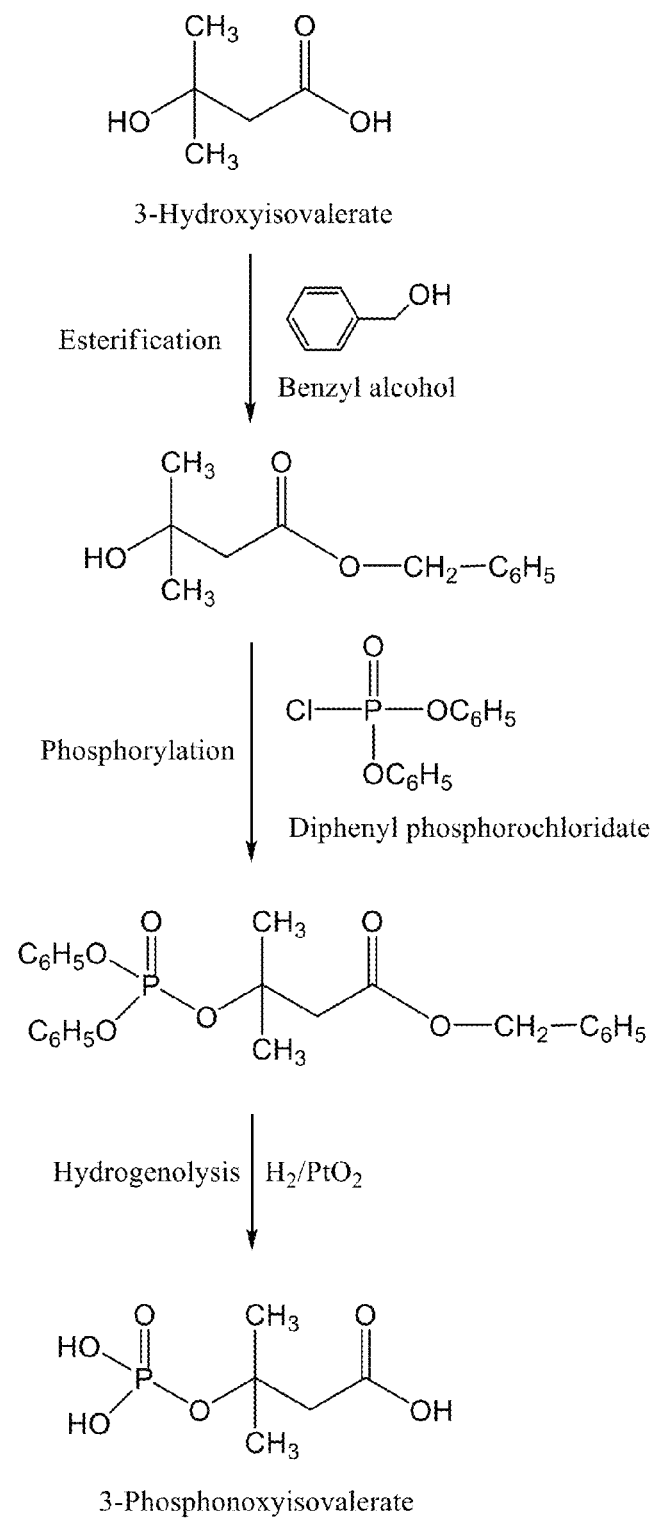

FIG. 13: Scheme for the chemical synthesis of 3-phosphonoxyisovalerate.

Figure 14:
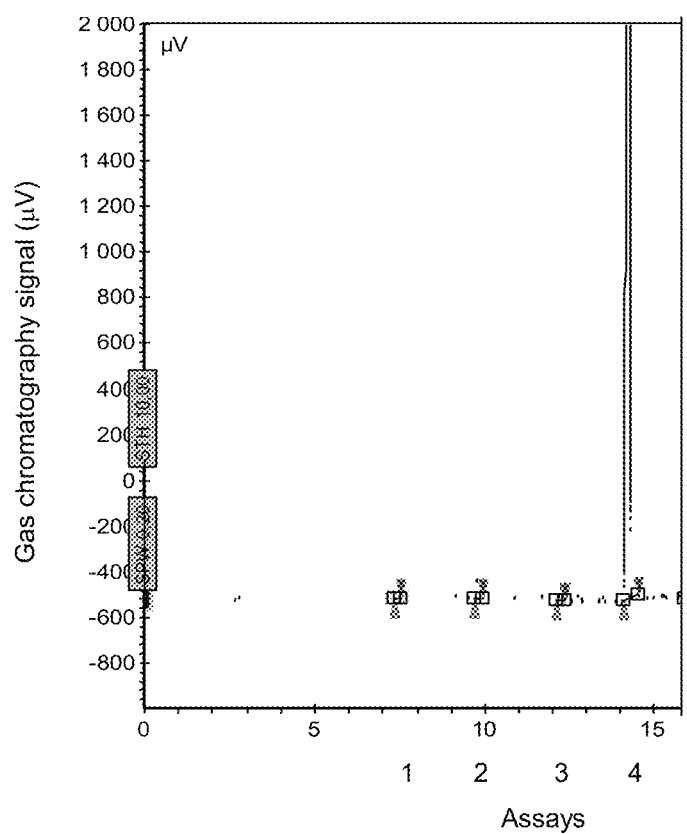

FIG. 14: GC analysis of assays for isobutene production from 3-phosphonoxyisovalerate in the absence and presence of ATP.

Assays:
1. Without enzyme, 0 mM ATP
2. 2 mg/ml enzyme, 0 mM ATP
3. Without enzyme, 10 mM ATP
4. 2 mg/ml enzyme, 10 mM ATP The following Examples serve to illustrate the invention.

EXAMPLES

Example 1

Cloning, Expression and Purification of an MDP Decarboxylase Library

A library of 55 genes encoding representatives of the diphosphomevalonate decarboxylase (MDP decarboxylase) family across eukaryotic, prokaryotic and archaeal organisms was constructed and tested to identify the most active candidates for improving isobutene (IBN) production.

Cloning, Bacterial Cultures and Expression of Proteins.

The genes encoding mevalonate diphosphate (MDP) decarboxylase EC 4.1.1.33 were cloned in the pET 25b vector (Novagen) in the case of eukaryotic genes and in pET 22b (Novagen) in the case of prokaryotic genes. A stretch of 6 histidine codons was inserted after the methionine initiation codon to provide an affinity tag for purification. Competent *E. coli* BL21(DE3) cells (Novagen) were transformed with these vectors according to the heat shock procedure. The transformed cells were grown with shaking (160 rpm) on ZYM-5052 auto-induction medium (Studier F W, *Prot. Exp. Pur.* 41, (2005), 207-234) for 6 h at 37° C. and protein expression was continued at 28° C. overnight (approximately 16 h). The cells were collected by centrifugation at 4° C., 10,000 rpm for 20 min and the pellets were frozen at −80° C.

Protein Purification and Concentration.

The pellets from 200 ml of culture cells were thawed on ice and resuspended in 5 ml of $Na_2HPO_4$ pH 8 containing 300 mM NaCl, 5 mM $MgCl_2$ and 1 mM DTT. Twenty microliters of lysonase (Novagen) were added. Cells were incubated 10 minutes at room temperature and then returned to ice for 20 minutes. Cell lysis was completed by sonication for 3×15 seconds. The bacterial extracts were then clarified by centrifugation at 4° C., 10,000 rpm for 20 min. The clarified bacterial lysates were loaded on PROTINO-1000 Ni-TED column (Macherey-Nagel) allowing adsorption of 6-His tagged proteins. Columns were washed and the enzymes of interest were eluted with 4 ml of 50 mM $Na_2HPO_4$ pH 8 containing 300 mM NaCl, 5 mM $MgCl_2$, 1 mM DTT, 250 mM imidazole. Eluates were then concentrated and desalted on Amicon Ultra-4 10 kDa filter unit (Millipore) and resuspended in 0.25 ml 50 mM Tris-HCl pH 7.4 containing 0.5 mM DTT and 5 mM $MgCl_2$. Protein concentrations were quantified according to the Bradford method. The purity of proteins thus purified varied from 40% to 90%.

Example 2

Screening of the MDP Decarboxylase Library

MDP decarboxylases were evaluated using a complementation assay. *P. torridus* MDP decarboxylase (SEQ ID NO:1) was incubated together with each tested enzyme from the library.

The enzymatic assay was carried out under the following conditions:

50 mM Tris HCl pH 7.0

10 mM $MgCl_2$ 20 mM KCl
40 mM ATP
50 mM 3-hydroxyisovalerate (HIV)
The pH was adjusted to 7.0
100 µg of the MDP decarboxylase from *P. torridus* (SEQ ID NO:1) and 1 mg of the MDP decarboxylase to be tested were added to 1 ml of reaction mixture. A reaction mixture containing only 100 µg of *P. torridus* MDP decarboxylase (SEQ ID NO:1) was used as reference. The mixture was then incubated without shaking at 45° C. for 90 h in a sealed vial (Interchim).

One ml of the gaseous phase was collected and injected into a HP5890 gas chromatograph (HP) equipped with an FID detector and a CP SilicaPlot column (Varian). Commercial isobutene was used as reference.

This screening procedure led to the identification of several MDP decarboxylase enzymes increasing the isobutene production rate. As shown in FIG. 7, a higher production of isobutene was observed for the following MDP decarboxylases.

Candidate 1:
  Accession number Genbank: CAI97800
  Accession number SwissProt/TrEMBL: Q1GAB2
  Organism: *Lactobacillus delbrueckii* subsp. *bulgaricus* ATCC 11842 (SEQ ID NO:9)
Candidate 2:
  Accession number Genbank: AAC50440.1
  Accession number SwissProt/TrEMBL: P53602.1
  Organism: *Homo sapiens* (SEQ ID NO:8)
Candidate 3:
  Accession number Genbank: ABV09606
  Accession number SwissProt/TrEMBL: A8AUU9
  Organism: *Streptococcus gordonii* str. Challis substr. CH1 (SEQ ID NO:6)

The highest production of isobutene was observed with purified MDP decarboxylase from *Streptococcus gordonii*.

This indicated that the two enzymes present in the assay (the one from *P. torridus* (SEQ ID NO:1) and the other from *S. gordonii* (SEQ ID NO:5)) were performing complementarily the two steps of reaction producing IBN from HIV: transfer of the terminal phosphoryl group from ATP to the C3-oxygen of 3-hydroxyisovalerate followed by combined dephosphorylation-decarboxylation of the intermediate 3-phosphonoxyisovalerate.

Example 3

Effect of Enzyme Concentration on Isobutene Production Yield

The effect of *Streptococcus gordonii* MDP decarboxylase (SEQ ID NO:5) concentration was assessed under the following conditions:
  50 mM Tris-HCl pH 7.0
  10 mM MgCl$_2$
  20 mM KCl
  40 mM ATP
  50 mM 3-hydroxyisovalerate (HIV)
The pH was adjusted to 7.0
100 µg of MDP decarboxylase from *P. torridus* (SEQ ID NO:1) and a varying amount (from 0 to 1 mg) of purified MDP decarboxylase from *Streptococcus gordonii* (SEQ ID NO:5) were added to 1 ml of reaction mixture. The mixture was then incubated without shaking at 45° C. for 90 h in a sealed vial (Interchim).

One ml of the headspace phase was collected and injected into a HP5890 gas chromatograph (HP) equipped with an FID detector and a CP SilicaPlot column (Varian). Commercial isobutene was used as reference.

Increasing the *S. gordonii* enzyme (SEQ ID NO:5) concentration resulted in an increase of the amount of isobutene produced (FIG. 8).

Example 4

Screening of a Library of *Streptococcus gordonii* MDP Decarboxylase Homologs

Using the BLAST online program hosted by NCBI, sequences were searched against non redundant protein sequence database to generate a list of enzymes with high sequence similarity (>40% identity) to the *Streptococcus gordonii* enzyme (SEQ ID NO:5). The resulting list included 18 candidates.

| Microorganisms | % Identity with MDP decarboxylase from *Streptococcus gordonii* | Accession number Genbank |
|---|---|---|
| *Streptococcus oralis* ATCC 35037 | 75 | EFE56694.1 |
| *Leptotrichia goodfellowii* F0264 | 61 | EEY36155.1 |
| *Carnobacterium* sp. AT7 | 40 | EDP67928.1 |
| *Enterococcus faecium* TX1330 | 40 | EEI60970.1 |
| *Staphylococcus aureus* JH1 | 40 | ABR51487.1 |
| *Streptococcus agalactiae* NEM316 | 70 | CAD47054.1 |
| *Streptococcus mutans* UA159 | 71 | AAN58642.1 |
| *Streptococcus uberis* 0140J | 71 | CAR41735.1 |
| *Streptococcus infantarius* subsp *infantarius* ATCC BAA-102 (SEQ ID NO: 7) | 71 | EDT48420.1 |
| *Streptococcus gallolyticus* UCN34 (SEQ ID NO: 11) | 71 | CBI13757.1 |
| *Streptococcus dysgalactiae* subsp *equisimilis* GGS_124 | 71 | BAH81333.1 |
| *Streptococcus* sp. M143 (SEQ ID NO: 13) | 76 | EFA24040.1 |
| *Streptococcus salivarius* SK126 (SEQ ID NO: 15) | 74 | EEK09252.1 |
| *Streptococcus suis* 89/1591 (SEQ ID NO: 14) | 40 | EEF63672.1 |
| *Streptococcus parasanguinis* ATCC 15912 | 73 | EFH19018.1 |
| *Streptococcus sanguinis* SK36 (SEQ ID NO: 12) | 98 | ABN43791.1 |
| *Streptococcus* sp. 2_1_36FAA | 98 | EEY81027.1 |
| *Streptococcus mitis* B6 (SEQ ID NO: 10) | 74 | CBJ22986.1 |

Sequences of MDP decarboxylase enzymes inferred from the genomes of the above species as well as from the genome of *S. gordonii* (SEQ ID NO:5) were generated by oligonucleotide concatenation to fit the codon usage of *E. coli*. A stretch of 6 histidine codons was inserted after the methionine initiation codon to provide an affinity tag for purification. The genes thus synthesized were cloned in a pET25b expression vector (the vectors were constructed by GENEART AG). After transformation of the *E. coli* strain BL21(DE3), the proteins were produced according to the protocol described in Example 1. The enzymes were then assayed using the method described in Example 2, using *Th. acidophilum* MDP decarboxylase (SEQ ID NO:2) instead of the *P. torridus* enzyme. This screening procedure led to the identification of enzymes more efficient for isobutene production than the *S. gordonii* enzyme (SEQ ID NO:5) (FIG. 9), in particular MDP decarboxylases from *S. infantarius* (SEQ ID NO:7), *S. gallolyticus* (SEQ ID NO:11), *S.* sp. M143 (SEQ ID NO:13), *S. salivarius*

(SEQ ID NO:15), *S. suis* (SEQ ID NO:14), *S. sanguinis* (SEQ ID NO:12) and *S. mitis* (SEQ ID NO:10).

Example 5

Characterisation of the Phosphotransferase Activity

The release of ADP that is associated with IBN production from HIV was quantified using the pyruvate kinase/lactate dehydrogenase coupled assay (FIG. 10). The MDP decarboxylases from *P. torridus* (SEQ ID NO:1), *Th. Acidophilum* (SEQ ID NO:2), *S. infantarius* (SEQ ID NO:7), *S. mitis* (SEQ ID NO:10) were evaluated for their ability to phosphorylate HIV, releasing ADP.

The studied enzymatic reaction was carried out under the following conditions at 40° C.:
50 mM Tris-HCl pH 7.0
10 mM $MgCl_2$
100 mM KCl
5 mM ATP
0.2 mM NADH
0.5 mM Phosphoenolpyruvate
3 U/ml Lactate dehydrogenase
1.5 U/ml Pyruvate kinase
0-50 mM 3-Hydroxyisovalerate (HIV)
The pH was adjusted to 7.0.

Each assay was started by addition of particular enzyme (at a concentration from 0.05 to 1 mg/ml) and the disappearance of NADH was monitored by following the absorbance at 340 nM.

Assays with MDP decarboxylases from the *P. torridus* phylum as well from the *Streptococcus* genus gave rise to a reproducible increase in ADP production in the presence of HIV. FIG. 11 shows an example of a Michaelis-Menten plot corresponding to the data collected for *P. torridus* enzyme. The kinetic parameters are shown in the following Table.

The enzymes from the *P. torridus* phylum displayed higher phosphotransferase activities than those of the *Streptococcus* genus.

Example 6

Isobutene Production from 3-Hydroxyisovalerate by Combining Two Enzymes

The desired enzymatic reaction was carried out under the following conditions:
50 mM Tris HCl pH 7.5
10 mM $MgCl_2$
20 mM KCl
40 mM ATP
50 mM HIV
The pH was adjusted to 7.5
100 µg of MDP decarboxylase from *Th. acidophilum* (SEQ ID NO:2) and 500 µg of

| Organism | $K_M$, mM | $k_{cat}$, $sec^{-1}$ | $k_{cat}/K_M \times 10^{-3}$, $mM^{-1} sec^{-1}$ |
|---|---|---|---|
| *Thermoplasma acidophilum* (SEQ ID NO: 2) | 4.02 | 0.26 | 60 |
| *Picrophilus torridus* (SEQ ID NO: 1) | 9.17 | 0.19 | 20 |
| *Streptococcus mitis* (SEQ ID NO: 10) | 12.1 | 0.04 | 3 |
| *Streptococcus infantarius* (SEQ ID NO: 7) | 13.4 | 0.03 | 2 |

MDP decarboxylase from *S. mitis* (SEQ ID NO:10) were added to 1 ml of reaction mixture. Control reactions with only one of the two enzymes were run in parallel. The assays were incubated without shaking at 37° C. in a sealed vial (Interchim).

The production of IBN was measured by analyzing aliquots sampled over a 142 hour incubation period.

One ml of the gaseous phase was collected and injected into a HP5890 gas chromatograph (HP) equipped with an FID detector and a CP SilicaPlot column (Varian). Commercial isobutene was used as reference.

The kinetics of isobutene production is shown in FIG. 12. MDP decarboxylase from *Th. acidophilum* (SEQ ID NO:2) catalyzed the production of isobutene from HIV. The addition of MDP decarboxylase from *S. mitis* (SEQ ID NO:10) led to a 3-fold increase of isobutene production after 142 h of incubation.

MDP decarboxylase from *S. mitis* (SEQ ID NO:10) alone produced only small amounts of isobutene after 6 days of incubation, indicating a low phosphotransferase activity.

Isobutene production can thus be increased by combining two types of enzymes performing complementarily the two reaction steps.

Example 7

Effect of ATP on Isobutene Production from 3-Phosphonoxyisovalerate (PIV)

The compound 3-phosphonoxyisovalerate (PIV) was chemically synthesized from 3-hydroxyisovalerate according to the scheme depicted in FIG. 13 by SYNTHEVAL (France).

The assays of isobutene production were carried out under the following conditions:
50 mM Tris-HCl pH 7.5
10 mM $MgCl_2$
20 mM KCl
0 mM ATP (assay No1 and No2)
10 mM ATP (assay No3 and No4)
25 mM 3-phosphonoxyisovalerate
The pH was adjusted to 7.5

The reaction was initiated by addition of 2 mg of purified MDP decarboxylase from *S. mitis* (SEQ ID NO:10) to 0.5 ml of reaction mixture. Control reactions were run in the absence of enzyme (assays No1 and No3).

The mixture was incubated without shaking at 37° C. for 26 h in a sealed vial of 2 ml (Interchim).

One ml of the gaseous phase was collected and injected into a Varian 430-GC gas chromatograph equipped with an FID detector and a CP SilicaPlot column (Varian). Commercial isobutene was used as reference.

Addition of 10 mM ATP to the reaction mixture increased 120 fold isobutene production from 3-phosphonoxyisovalerate (PIV) (FIG. 14).

Example 8

Kinetic Parameters of Isobutene Production from 3-Phosphonoxyisovalerate (PIV)

The kinetic parameters of isobutene production were measured under the following conditions:
50 mM Tris-HCl pH 7.5
10 mM $MgCl_2$
50 mM KCl
40 mM ATP
0-100 mM 3-phosphonoxyisovalerate
The pH was adjusted to 7.5
The reaction was initiated by addition of 1 mg of purified MDP decarboxylase from *S. mitis* (SEQ ID NO:10) to 0.5 ml of reaction mixture. The mixture was then incubated without shaking at 37° C. for 44 h in a sealed vial of 2 ml (Interchim).

One ml of the gaseous phase was collected and injected into a Varian 430-GC gas chromatograph equipped with an FID detector and a CP SilicaPlot column (Varian). Commercial isobutene was used as reference.

The assays with MDP decarboxylase from *S. mitis* (SEQ ID NO:10) showed a 160-400 fold increase in IBN production over the background level (spontaneous decomposition of 3-phosphonoxyisovalerate) in the presence of ATP as cofactor (see the following Table).

|                       | Peak area, arbitrary units |                |
| --------------------- | -------------------------- | -------------- |
| PIV concentration, mM | No enzyme                  | 2 mg/ml enzyme |
| 25                    | 164.9                      | 26945.2        |
| 50                    | 328.7                      | 65720.4        |
| 75                    | 561.5                      | 239249.2       |
| 100                   | 2078.7                     | 339363.7       |

MDP decarboxylase from *S. mitis* (SEQ ID NO:10) was found to have a $K_M$ higher than 60 mM and a $k_{cat}$ of at least $1.3 \times 10^{-3}$ sec$^{-1}$.

---

The invention claimed is:

1. A method for producing an alkene from 3-hydroxyalkanoate comprising culturing under conditions to allow for the conversion of 3-hydroxyalkanoate to the alkene a recombinant microorganism or plant cell overexpressing a first and a second heterologous enzyme as compared to the unmodified microorganism or plant cell, wherein:
   (i) said first heterologous enzyme is a mevalonate diphosphate (MDP) decarboxylase and has an activity of converting the 3-hydroxyalkanoate into the corresponding 3-phosphonoxyalkanoate; and
   (ii) said second heterologous enzyme is a mevalonate diphosphate (MDP) decarboxylase and is different from the first heterologous enzyme and has an activity of converting said 3-phosphonoxyalkanoate into said alkene
   and wherein the production of the alkene is increased as compared to a recombinant microorganism expressing only the first or the second heterologous enzyme.

2. The method of claim 1 wherein the first heterologous enzyme is a protein comprising the amino acid sequence as shown in SEQ ID NO: 2 or the second heterologous enzyme is a protein comprising the amino acid sequence as shown in SEQ ID NO: 10.

3. The method of claim 2, wherein the first heterologous enzyme is a protein comprising the amino acid sequence as shown in SEQ ID NO: 2 and the second heterologous enzyme is a protein comprising the amino acid sequence as shown in SEQ ID NO: 10.

4. The method of claim 1, wherein the 3-hydroxyalkanoate is 3-hydroxypropionate and the alkene is ethylene.

5. The method of claim 1, wherein the 3-hydroxyalkanoate is 3-hydroxybutyrate and the alkene is propylene.

6. The method of claim 1, wherein the 3-hydroxyalkanoate is 3-hydroxyvalerate and the alkene is 1-butylene.

7. The method of claim 1, wherein the hydroxyalkanoate is 3-hydroxy-3-methylbutyrate and the alkene is isobutylene.

8. The method of claim 1, wherein the 3-hydroxyalkanoate is 3-hydroxy-3-methylvalerate and the alkene is isoamylene.

9. The method of claim 1 wherein the microorganism is a bacterium, a fungus, a yeast or a microalgae.

10. The method of claim 1, wherein the method is carried out in a plant cell.

11. The method of claim 1, comprising a step of collecting gaseous alkenes degassing out of the reaction.

12. The method of claim 1, wherein the method is carried out with ATP, dATP, ADP, AMP, an NTP other than ATP, a dNTP or pyrophosphate as co-substrate.

13. The method of claim 1 wherein the first heterologous enzyme is selected from:
   (A) a protein comprising the amino acid sequence as shown in SEQ ID NO: 1;
   (B) a protein comprising the amino acid sequence as shown in SEQ ID NO: 3; or (C) a protein comprising the amino acid sequence as shown in SEQ ID NO: 4.

14. The method of claim 1 wherein the second heterologous enzyme is selected from:
(A) a protein comprising the amino acid sequence as shown in SEQ ID NO: 5;
(B) a protein comprising the amino acid sequence as shown in SEQ ID NO: 6;
(C) a protein comprising the amino acid sequence as shown in SEQ ID NO: 7;
(D) a protein comprising the amino acid sequence as shown in SEQ ID NO: 8;
(E) a protein comprising the amino acid sequence as shown in SEQ ID NO: 9;
(F) a protein comprising the amino acid sequence as shown in SEQ ID NO: 11;
(G) a protein comprising the amino acid sequence as shown in SEQ ID NO: 12;
(H) a protein comprising the amino acid sequence as shown in SEQ ID NO: 13;
(I) a protein comprising the amino acid sequence as shown in SEQ ID NO: 14; or
(J) a protein comprising the amino acid sequence as shown in SEQ ID NO: 15.

15. The method of claim 1 wherein:
(i) the first heterologous enzyme is selected from:
 (A) a protein comprising the amino acid sequence as shown in SEQ ID NO: 1;
 (B) a protein comprising the amino acid sequence as shown in SEQ ID NO: 3; or
 (C) a protein comprising the amino acid sequence as shown in SEQ ID NO: 4; and
(ii) the second heterologous enzyme is selected from:
 (A) a protein comprising the amino acid sequence as shown in SEQ ID NO: 5;
 (B) a protein comprising the amino acid sequence as shown in SEQ ID NO: 6;
 (C) a protein comprising the amino acid sequence as shown in SEQ ID NO: 7;
 (D) a protein comprising the amino acid sequence as shown in SEQ ID NO: 8;
 (E) a protein comprising the amino acid sequence as shown in SEQ ID NO: 9;
 (F) a protein comprising the amino acid sequence as shown in SEQ ID NO: 11;
 (G) a protein comprising the amino acid sequence as shown in SEQ ID NO: 12;
 (H) a protein comprising the amino acid sequence as shown in SEQ ID NO: 13;
 (I) a protein comprising the amino acid sequence as shown in SEQ ID NO: 14; or
 (J) a protein comprising the amino acid sequence as shown in SEQ ID NO: 15.

16. A method for producing an alkene from 3-hydroxyalkanoate under conditions to allow for the conversion of 3-hydroxyalkanoate to the alkene using a first enzyme and a second enzyme in an in vitro cell-free system, wherein:
(i) said first enzyme is a mevalonate diphosphate (MDP) decarboxylase and has an activity of converting the 3-hydroxyalkanoate into the corresponding 3-phosphonoxyalkanoate; and
(ii) said second enzyme is a mevalonate diphosphate (MDP) decarboxylase and is different from the first enzyme and has an activity of converting said 3-phosphonoxyalkanoate into said alkene
wherein the production of the alkene is increased as compared to use of only the first or the second enzyme.

17. The method of claim 16 wherein the first enzyme is a protein comprising the amino acid sequence as shown in SEQ ID NO: 2 or the second enzyme is a protein comprising the amino acid sequence as shown in SEQ ID NO: 10.

18. The method of claim 16, wherein the first enzyme is a protein comprising the amino acid sequence as shown in SEQ ID NO: 2 and the second enzyme is a protein comprising the amino acid sequence as shown in SEQ ID NO: 10.

19. The method of claim 16, wherein the 3-hydroxyalkanoate is 3-hydroxypropionate and the alkene is ethylene.

20. The method of claim 16, wherein the 3-hydroxyalkanoate is 3-hydroxybutyrate and the alkene is propylene.

21. The method of claim 16, wherein the 3-hydroxyalkanoate is 3-hydroxyvalerate and the alkene is 1-butylene.

22. The method of claim 16, wherein the hydroxyalkanoate is 3-hydroxy-3-methylbutyrate and the alkene is isobutylene.

23. The method of claim 16, wherein the 3-hydroxyalkanoate is 3-hydroxy-3-methylvalerate and the alkene is isoamylene.

24. The method of claim 16, comprising a step of collecting gaseous alkenes degassing out of the reaction.

25. The method of claim 16, wherein the method is carried out with ATP, dATP, ADP, AMP, an NTP other than ATP, a dNTP or pyrophosphate as co-substrate.

26. The method of claim 16 wherein the first enzyme is selected from:
(A) a protein comprising the amino acid sequence as shown in SEQ ID NO: 1;
(B) a protein comprising the amino acid sequence as shown in SEQ ID NO: 3; or
(C) a protein comprising the amino acid sequence as shown in SEQ ID NO: 4.

27. The method of claim 16 wherein the second enzyme is selected from:
(A) a protein comprising the amino acid sequence as shown in SEQ ID NO: 5;
(B) a protein comprising the amino acid sequence as shown in SEQ ID NO: 6;
(C) a protein comprising the amino acid sequence as shown in SEQ ID NO: 7;
(D) a protein comprising the amino acid sequence as shown in SEQ ID NO: 8;
(E) a protein comprising the amino acid sequence as shown in SEQ ID NO: 9;
(F) a protein comprising the amino acid sequence as shown in SEQ ID NO: 11;
(G) a protein comprising the amino acid sequence as shown in SEQ ID NO: 12;
(H) a protein comprising the amino acid sequence as shown in SEQ ID NO: 13;
(I) a protein comprising the amino acid sequence as shown in SEQ ID NO: 14; or
(J) a protein comprising the amino acid sequence as shown in SEQ ID NO: 15.

28. The method of claim 16 wherein:
(i) the first enzyme is selected from:
 (A) a protein comprising the amino acid sequence as shown in SEQ ID NO: 1;
 (B) a protein comprising the amino acid sequence as shown in SEQ ID NO: 3; or
 (C) a protein comprising the amino acid sequence as shown in SEQ ID NO: 4; and
(ii) the second enzyme is selected from:
 (A) a protein comprising the amino acid sequence as shown in SEQ ID NO: 5;
 (B) a protein comprising the amino acid sequence as shown in SEQ ID NO: 6;

(C) a protein comprising the amino acid sequence as shown in SEQ ID NO: 7;
(D) a protein comprising the amino acid sequence as shown in SEQ ID NO: 8;
(E) a protein comprising the amino acid sequence as shown in SEQ ID NO: 9;
(F) a protein comprising the amino acid sequence as shown in SEQ ID NO: 11;
(G) a protein comprising the amino acid sequence as shown in SEQ ID NO: 12;
(H) a protein comprising the amino acid sequence as shown in SEQ ID NO: 13;
(I) a protein comprising the amino acid sequence as shown in SEQ ID NO: 14; or
(J) a protein comprising the amino acid sequence as shown in SEQ ID NO: 15.

* * * * *

SEQUENCE LISTING

<160> NUMBER OF SEQ ID NOS: 15

<210> SEQ ID NO 1
<211> LENGTH: 324
<212> TYPE: PRT
<213> ORGANISM: Picrophilus torridus

<400> SEQUENCE: 1

```
Met Glu Asn Tyr Asn Val Lys Thr Arg Ala Phe Pro Thr Ile Gly Ile
1               5                   10                  15

Ile Leu Leu Gly Gly Ile Ser Asp Lys Lys Asn Arg Ile Pro Leu His
            20                  25                  30

Thr Thr Ala Gly Ile Ala Tyr Thr Gly Ile Asn Asn Asp Val Tyr Thr
        35                  40                  45

Glu Thr Lys Leu Tyr Val Ser Lys Asp Glu Lys Cys Tyr Ile Asp Gly
    50                  55                  60

Lys Glu Ile Asp Leu Asn Ser Asp Arg Ser Pro Ser Lys Val Ile Asp
65                  70                  75                  80

Lys Phe Lys His Glu Ile Leu Met Arg Val Asn Leu Asp Asp Glu Asn
                85                  90                  95

Asn Leu Ser Ile Asp Ser Arg Asn Phe Asn Ile Leu Ser Gly Ser Ser
            100                 105                 110

Asp Ser Gly Ala Ala Ala Leu Gly Glu Cys Ile Glu Ser Ile Phe Glu
        115                 120                 125

Tyr Asn Ile Asn Ile Phe Thr Phe Glu Asn Asp Leu Gln Arg Ile Ser
    130                 135                 140

Glu Ser Val Gly Arg Ser Leu Tyr Gly Gly Leu Thr Val Asn Tyr Ala
145                 150                 155                 160

Asn Gly Arg Glu Ser Leu Thr Glu Pro Leu Leu Glu Pro Glu Ala Phe
                165                 170                 175

Asn Asn Phe Thr Ile Ile Gly Ala His Phe Asn Ile Asp Arg Lys Pro
            180                 185                 190

Ser Asn Glu Ile His Glu Asn Ile Ile Lys His Glu Asn Tyr Arg Glu
        195                 200                 205

Arg Ile Lys Ser Ala Glu Arg Lys Ala Lys Lys Leu Glu Glu Leu Ser
    210                 215                 220

Arg Asn Ala Asn Ile Lys Gly Ile Phe Glu Leu Ala Glu Ser Asp Thr
225                 230                 235                 240
```

```
Val Glu Tyr His Lys Met Leu His Asp Val Gly Val Asp Ile Ile Asn
                245                 250                 255

Asp Arg Met Glu Asn Leu Ile Glu Arg Val Lys Glu Met Lys Asn Asn
            260                 265                 270

Phe Trp Asn Ser Tyr Ile Val Thr Gly Gly Pro Asn Val Phe Val Ile
        275                 280                 285

Thr Glu Lys Lys Asp Val Asp Lys Ala Met Glu Gly Leu Asn Asp Leu
    290                 295                 300

Cys Asp Asp Ile Arg Leu Leu Lys Val Ala Gly Lys Pro Gln Val Ile
305                 310                 315                 320

Ser Lys Asn Phe

<210> SEQ ID NO 2
<211> LENGTH: 318
<212> TYPE: PRT
<213> ORGANISM: Thermoplasma acidophilum

<400> SEQUENCE: 2

Met Thr Tyr Arg Ser Ile Gly Ser Thr Ala Tyr Pro Thr Ile Gly Val
1               5                   10                  15

Val Leu Leu Gly Gly Ile Ala Asn Pro Val Thr Arg Thr Pro Leu His
            20                  25                  30

Thr Ser Ala Gly Ile Ala Tyr Ser Asp Ser Cys Gly Ser Ile Arg Ser
        35                  40                  45

Glu Thr Arg Ile Tyr Ala Asp Glu Ala Thr His Ile Tyr Phe Asn Gly
    50                  55                  60

Thr Glu Ser Thr Asp Asp Asn Arg Ser Val Arg Arg Val Leu Asp Arg
65                  70                  75                  80

Tyr Ser Ser Val Phe Glu Glu Ala Phe Gly Thr Lys Thr Val Ser Tyr
                85                  90                  95

Ser Ser Gln Asn Phe Gly Ile Leu Ser Gly Ser Ser Asp Ala Gly Ala
            100                 105                 110

Ala Ser Ile Gly Ala Ala Ile Leu Gly Leu Lys Pro Asp Leu Asp Pro
        115                 120                 125

His Asp Val Glu Asn Asp Leu Arg Ala Val Ser Glu Ser Ala Gly Arg
    130                 135                 140

Ser Leu Phe Gly Gly Leu Thr Ile Thr Trp Ser Asp Gly Phe His Ala
145                 150                 155                 160

Tyr Thr Glu Lys Ile Leu Asp Pro Glu Ala Phe Ser Gly Tyr Ser Ile
                165                 170                 175

Val Ala Phe Ala Phe Asp Tyr Gln Arg Asn Pro Ser Asp Val Ile His
            180                 185                 190

Gln Asn Ile Val Arg Ser Asp Leu Tyr Pro Ala Arg Lys Lys His Ala
        195                 200                 205

Asp Glu His Ala His Met Ile Lys Glu Tyr Ala Lys Thr Asn Asp Ile
    210                 215                 220

Lys Gly Ile Phe Asp Leu Ala Gln Glu Asp Thr Glu Glu Tyr His Ser
225                 230                 235                 240

Ile Leu Arg Gly Val Gly Val Asn Val Ile Arg Glu Asn Met Gln Lys
                245                 250                 255

Leu Ile Ser Tyr Leu Lys Leu Ile Arg Lys Asp Tyr Trp Asn Ala Tyr
            260                 265                 270

Ile Val Thr Gly Gly Ser Asn Val Tyr Val Ala Val Glu Ser Glu Asn
        275                 280                 285
```

```
Ala Asp Arg Leu Phe Ser Ile Glu Asn Thr Phe Gly Ser Lys Lys Lys
        290                 295                 300

Met Leu Arg Ile Val Gly Gly Ala Trp His Arg Arg Pro Glu
305                 310                 315

<210> SEQ ID NO 3
<211> LENGTH: 320
<212> TYPE: PRT
<213> ORGANISM: Thermoplasma volcanium

<400> SEQUENCE: 3

Met Ser Asn Ser Ser Ile Thr Ser Val Ala Tyr Pro Thr Ile Gly Val
1               5                   10                  15

Val Leu Gly Gly Ile Ala Asn Glu Lys Thr Arg Thr Pro Leu His
            20                  25                  30

Thr Ser Ala Gly Ile Ala Tyr Thr Asp Ser Cys Gly Ser Ile Arg Thr
            35                  40                  45

Glu Ser Thr Ile Tyr Gly Asp Ser Glu Met His Ile Tyr Phe Asn Gly
    50                  55                  60

Thr Glu Ser Lys Asp Glu Asn Arg Ser Val Lys Ser Val Leu Glu Arg
65                  70                  75                  80

Tyr Arg Asn Glu Leu Gln Ser Phe Phe Gly Lys Lys Asp Val Ser Tyr
                85                  90                  95

Ser Ser Leu Asn Tyr Gly Ile Leu Ser Gly Ser Ser Asp Ala Gly Ala
            100                 105                 110

Ala Ser Ile Gly Ala Ile Leu Ser Phe Ile Asp Lys Lys Asn Asp Ile
        115                 120                 125

His Asp Ile Glu Asn Asp Ile Arg Met Ile Ser Glu Ser Ala Gly Arg
130                 135                 140

Ser Leu His Gly Gly Leu Thr Ile Thr Trp Ser Asp Gly Tyr Ser Ala
145                 150                 155                 160

Tyr Thr Glu Arg Val Leu Gly Pro Glu His Phe Asn Asn Tyr Ala Ile
                165                 170                 175

Val Gly Phe Ser Phe Asp Tyr Pro Arg Asn Pro Ser Asp Thr Ile His
            180                 185                 190

Gln Asn Ile Ile Lys Ser Lys Arg Tyr Lys Gln Arg Thr Ile Asp Ala
        195                 200                 205

Asp Glu His Ala His Glu Ile Lys Glu Met Ala Arg Thr Asp Asp Ile
210                 215                 220

Glu Gly Ile Phe Glu Lys Ala Glu Glu Asp Thr Glu Glu Tyr His Ser
225                 230                 235                 240

Ile Leu Arg Glu Val Gly Val Leu Val Ile Arg Glu Asn Met Gln Lys
                245                 250                 255

Leu Ile Glu Phe Ile Lys Ile Leu Arg Lys Glu Phe Trp Asn Ser Tyr
            260                 265                 270

Ile Val Thr Gly Gly Ser Asn Val Tyr Ile Val Arg Arg Asp Asp
        275                 280                 285

Leu Glu Arg Leu Ile His Ile Lys Asn Thr Phe Gly Ser Lys Pro Lys
290                 295                 300

Ile Leu Asn Val Ala Gly Pro Ala Trp Ile Lys Lys Val Glu Ser Asp
305                 310                 315                 320

<210> SEQ ID NO 4
<211> LENGTH: 322
<212> TYPE: PRT
```

<213> ORGANISM: Ferroplasma acidarmanus fer1

<400> SEQUENCE: 4

Met Glu Lys Tyr Tyr Val Glu Val Lys Ala Tyr Pro Thr Ile Gly Ile
1               5                   10                  15

Leu Leu Leu Gly Gly Val Ser Asp Asn Lys Lys Arg Leu Pro Arg His
            20                  25                  30

Thr Thr Ala Gly Ile Ala Tyr Thr Gly Leu Asp Asp Ile Tyr Val
        35                  40                  45

Lys Thr Asp Leu Tyr Leu Ser Asn Gln Lys Ser Gly Ile Ile Asn Gly
    50                  55                  60

Lys Glu Val Ser Pro Asp Ser Pro Arg Ser Pro Phe Val Val Ile Asp
65                  70                  75                  80

Lys Tyr Arg His Glu Ile Leu Met Arg His Pro Glu Tyr Ser Glu Val
                85                  90                  95

Ser Phe Val Ser Glu Asn Lys Asn Val Ile Ser Gly Ser Ser Asp Ala
            100                 105                 110

Gly Ala Ala Ala Ile Gly Glu Cys Ile Gln Ser Ile Phe Glu Tyr Asn
        115                 120                 125

Ile Asn Ile Phe Asn Phe Glu Asn Asp Leu Gln Gln Ile Ser Glu Ser
130                 135                 140

Ala Gly Arg Ser Met Phe Gly Gly Phe Thr Ile Asn His Ala Asn Gly
145                 150                 155                 160

Lys Glu Ser Leu Thr Asp Glu Ile Leu Gly Pro Glu Asp Phe Glu Asp
                165                 170                 175

Phe Val Ile Val Ala Cys Lys Phe Ser Glu Asp Arg Lys Pro Ser Asp
            180                 185                 190

Thr Ile His Ser Asn Ile Ile Asn His Glu Lys Tyr Ala Glu Arg Val
        195                 200                 205

Lys Asn Ser Glu Leu Arg Ala Lys Glu Leu Glu Lys Met Ala Asp Ser
210                 215                 220

Gly Asp Ile Lys Gly Ile Phe Glu Ala Gly Glu Lys Asp Thr Gln Glu
225                 230                 235                 240

Tyr His Ser Met Leu Arg Glu Val Gly Val Ser Ile Ile Thr Asp Glu
                245                 250                 255

Met Gln Arg Leu Ile Glu Lys Val Glu Glu Leu Lys Ala Glu Phe Trp
            260                 265                 270

Asn Ala Tyr Ile Val Thr Gly Gly Thr Asn Val Phe Val Ala Val Glu
        275                 280                 285

Arg Lys Asn Met Glu Lys Met Lys Asn Ala Ala Met Glu Phe Lys Cys
        290                 295                 300

Thr Pro Val Tyr Leu Lys Val Ala Gly Lys Pro Asp Val Ile Ser Lys
305                 310                 315                 320

Asn Phe

<210> SEQ ID NO 5
<211> LENGTH: 315
<212> TYPE: PRT
<213> ORGANISM: Streptococcus gordonii

<400> SEQUENCE: 5

Met Asp Arg Lys Pro Val Ser Val Lys Ser Tyr Ala Asn Ile Ala Ile
1               5                   10                  15

Val Lys Tyr Trp Gly Lys Lys Asp Ala Glu Lys Met Ile Pro Ser Thr
            20                  25                  30

```
Ser Ser Ile Ser Leu Thr Leu Glu Asn Met Tyr Thr Glu Thr Gln Leu
        35                  40                  45

Ser Pro Leu Pro Ala Thr Ala Thr Gly Asp Glu Phe Tyr Ile Asp Gly
    50                  55                  60

Gln Leu Gln Ser Pro Ala Glu His Thr Lys Ile Ser Lys Ile Ile Asp
65                  70                  75                  80

Arg Phe Arg Ser Pro Glu Asp Gly Phe Val Arg Val Asp Thr Ser Asn
                85                  90                  95

Asn Met Pro Thr Ala Ala Gly Leu Ser Ser Ser Ser Gly Leu Ser
                100                 105                 110

Ala Leu Val Lys Ala Cys Asn Ala Tyr Phe Gln Thr Gly Tyr Gln Ala
            115                 120                 125

Gln Glu Leu Ala Gln Leu Ala Lys Phe Ala Ser Gly Ser Ser Ala Arg
    130                 135                 140

Ser Phe Phe Gly Pro Leu Ala Ala Trp Asp Lys Asp Ser Gly Ala Ile
145                 150                 155                 160

Tyr Pro Val Lys Thr Asp Leu Lys Leu Ala Met Ile Met Leu Val Leu
                165                 170                 175

His Asp Glu Lys Lys Pro Ile Ser Ser Arg Asp Gly Met Glu Leu Cys
            180                 185                 190

Ala Lys Thr Ser Thr Ile Phe Pro Asp Trp Ile Ala Gln Ser Ala Leu
    195                 200                 205

Asp Tyr Gln Ala Met Leu Ala Tyr Leu Arg Asp Asn Glu Phe Ala Lys
210                 215                 220

Val Gly Gln Leu Thr Glu Asn Ala Leu Arg Met His Ala Thr Thr
225                 230                 235                 240

Glu Lys Ala Tyr Pro Pro Phe Ser Tyr Leu Thr Glu Glu Ser Tyr Gln
                245                 250                 255

Ala Met Asp Ala Val Arg Lys Leu Arg Glu Gln Gly Glu Arg Cys Tyr
            260                 265                 270

Phe Thr Met Asp Ala Gly Pro Asn Val Lys Val Leu Cys Leu Glu Glu
    275                 280                 285

Asp Leu Asp His Leu Ala Ala Ile Leu Glu Lys Asp Tyr Arg Leu Ile
290                 295                 300

Val Ser Lys Thr Lys Asp Leu Ser Asp Glu Ser
305                 310                 315

<210> SEQ ID NO 6
<211> LENGTH: 315
<212> TYPE: PRT
<213> ORGANISM: Streptococcus gordonii str. Challis substr. CH1

<400> SEQUENCE: 6

Met Asp Arg Lys Pro Val Ser Val Lys Ser Tyr Ala Asn Ile Ala Ile
1               5                   10                  15

Val Lys Tyr Trp Gly Lys Lys Asp Ala Glu Lys Met Ile Pro Ser Thr
            20                  25                  30

Ser Ser Ile Ser Leu Thr Leu Glu Asn Met Tyr Thr Glu Thr Gln Leu
        35                  40                  45

Ser Pro Leu Pro Asp Thr Ala Thr Gly Asp Glu Phe Tyr Ile Asp Gly
    50                  55                  60

Gln Leu Gln Ser Pro Ala Glu His Ala Lys Ile Ser Lys Ile Ile Asp
65                  70                  75                  80

Arg Phe Arg Ser Pro Glu Asp Gly Phe Val Arg Val Asp Thr Ser Asn
```

```
            85                  90                  95
Asn Met Pro Thr Ala Ala Gly Leu Ser Ser Ser Ser Gly Leu Ser
            100                 105                 110

Ala Leu Val Lys Ala Cys Asn Ala Tyr Phe Gln Thr Gly Tyr Gln Thr
            115                 120                 125

Glu Glu Leu Ala Gln Leu Ala Lys Phe Ala Ser Gly Ser Ser Ala Arg
            130                 135                 140

Ser Phe Phe Gly Pro Leu Ala Ala Trp Asp Lys Asp Ser Gly Ala Ile
145                 150                 155                 160

Tyr Pro Val Lys Thr Asp Leu Lys Leu Ala Met Ile Met Leu Val Leu
                165                 170                 175

His Asp Glu Lys Lys Pro Ile Ser Ser Arg Asp Gly Met Glu Leu Cys
                180                 185                 190

Ala Lys Thr Ser Thr Ile Phe Pro Asp Trp Ile Ala Gln Ser Ala Leu
                195                 200                 205

Asp Tyr Gln Ala Met Leu Gly Tyr Leu Gln Asp Asn Asp Phe Ala Lys
                210                 215                 220

Val Gly Gln Leu Thr Glu Glu Asn Ala Leu Arg Met His Ala Thr Thr
225                 230                 235                 240

Glu Lys Ala Tyr Pro Pro Phe Ser Tyr Leu Thr Glu Glu Ser Tyr Gln
                245                 250                 255

Ala Met Asp Ala Val Arg Lys Leu Arg Glu Gln Gly Leu Arg Cys Tyr
                260                 265                 270

Phe Thr Met Asp Ala Gly Pro Asn Val Lys Val Leu Cys Leu Glu Glu
                275                 280                 285

Asp Leu Asp His Leu Ala Ala Ile Phe Glu Lys Asp Tyr Arg Leu Ile
                290                 295                 300

Val Ser Lys Thr Lys Asp Leu Ser Asp Glu Ser
305                 310                 315

<210> SEQ ID NO 7
<211> LENGTH: 311
<212> TYPE: PRT
<213> ORGANISM: Streptococcus infantarius subsp infantarius ATCC BAA-102

<400> SEQUENCE: 7

Met Asp Arg Lys Ile Val Thr Val Lys Ser Tyr Ala Asn Ile Ala Ile
1               5                   10                  15

Ile Lys Tyr Trp Gly Lys Ala Asp Ala Ala Lys Met Ile Pro Ala Thr
                20                  25                  30

Ser Ser Ile Ser Leu Thr Leu Glu Asn Met Phe Thr Thr Thr Ser Val
            35                  40                  45

Ser Phe Leu Pro Asp Ser Ala Ser His Asp Glu Phe Tyr Ile Asn Gly
            50                  55                  60

Val Leu Gln Asp Asp Lys Glu His Ala Lys Ile Ser Ala Ile Ile Asp
65                  70                  75                  80

Gln Tyr Arg Gly Gln Arg Ser Glu Tyr Val Lys Val Glu Thr Ser Asn
                85                  90                  95

Asn Met Pro Thr Ala Ala Gly Leu Ser Ser Ser Ser Gly Leu Ser
            100                 105                 110

Ala Leu Val Lys Ala Cys Asn Glu Leu Phe Glu Thr Gly Leu Thr Arg
            115                 120                 125

Ala Glu Leu Ala Gln Lys Ala Lys Phe Ala Ser Gly Ser Ser Ser Arg
            130                 135                 140
```

```
Ser Phe Phe Gly Pro Leu Ala Ala Trp Asp Lys Asp Ser Gly Glu Val
145                 150                 155                 160

Tyr Pro Val Gln Thr Asp Leu Lys Leu Ala Met Ile Met Leu Val Leu
                165                 170                 175

Ser Asp Ser Lys Lys Ser Ile Ser Ser Arg Glu Gly Met Lys Arg Cys
            180                 185                 190

Val Glu Thr Ser Thr Thr Phe Ala Asp Trp Val Lys Gln Ser Glu Gln
        195                 200                 205

Asp Tyr Lys Asp Met Leu Gly Tyr Leu Lys Asn Asn Asp Phe Glu Arg
    210                 215                 220

Val Gly Glu Leu Thr Glu Arg Asn Ala Leu Ala Met His Asp Thr Asn
225                 230                 235                 240

Thr His Ala Asn Pro Pro Phe Asn Tyr Leu Thr Glu Glu Ser Tyr Lys
                245                 250                 255

Ala Met Glu Phe Val Lys Gln Leu Arg Ser Glu Gly Glu Lys Cys Tyr
            260                 265                 270

Phe Thr Met Asp Ala Gly Pro Asn Val Lys Val Leu Cys Leu Glu Glu
        275                 280                 285

Asp Leu Glu Arg Leu Thr Lys Arg Phe Glu Glu Asn Tyr Arg Val Ile
    290                 295                 300

Val Ser Arg Thr Lys Glu Leu
305                 310

<210> SEQ ID NO 8
<211> LENGTH: 400
<212> TYPE: PRT
<213> ORGANISM: Homo sapiens

<400> SEQUENCE: 8

Met Ala Ser Glu Lys Pro Leu Ala Ala Val Thr Cys Thr Ala Pro Val
1               5                   10                  15

Asn Ile Ala Val Ile Lys Tyr Trp Gly Lys Arg Asp Glu Glu Leu Val
            20                  25                  30

Leu Pro Ile Asn Ser Ser Leu Ser Val Thr Leu His Gln Asp Gln Leu
        35                  40                  45

Lys Thr Thr Thr Thr Ala Val Ile Ser Lys Asp Phe Thr Glu Asp Arg
    50                  55                  60

Ile Trp Leu Asn Gly Arg Glu Glu Asp Val Gly Gln Pro Arg Leu Gln
65                  70                  75                  80

Ala Cys Leu Arg Glu Ile Arg Cys Leu Ala Arg Lys Arg Arg Asn Ser
                85                  90                  95

Arg Asp Gly Asp Pro Leu Pro Ser Ser Leu Ser Cys Lys Val His Val
            100                 105                 110

Ala Ser Val Asn Asn Phe Pro Thr Ala Ala Gly Leu Ala Ser Ser Ala
        115                 120                 125

Ala Gly Tyr Ala Cys Leu Ala Tyr Thr Leu Ala Arg Val Tyr Gly Val
    130                 135                 140

Glu Ser Asp Leu Ser Glu Val Ala Arg Arg Gly Ser Gly Ser Ala Cys
145                 150                 155                 160

Arg Ser Leu Tyr Gly Gly Phe Val Glu Trp Gln Met Gly Glu Gln Ala
                165                 170                 175

Asp Gly Lys Asp Ser Ile Ala Arg Gln Val Ala Pro Glu Ser His Trp
            180                 185                 190

Pro Glu Leu Arg Val Leu Ile Leu Val Val Ser Ala Glu Lys Lys Leu
        195                 200                 205
```

```
Thr Gly Ser Thr Val Gly Met Arg Ala Ser Val Glu Thr Ser Pro Leu
            210                 215                 220

Leu Arg Phe Arg Ala Glu Ser Val Val Pro Ala Arg Met Ala Glu Met
225                 230                 235                 240

Ala Arg Cys Ile Arg Glu Arg Asp Phe Pro Ser Phe Ala Gln Leu Thr
                245                 250                 255

Met Lys Asp Ser Asn Gln Phe His Ala Thr Cys Leu Asp Thr Phe Pro
            260                 265                 270

Pro Ile Ser Tyr Leu Asn Ala Ile Ser Trp Arg Ile Ile His Leu Val
        275                 280                 285

His Arg Phe Asn Ala His His Gly Asp Thr Lys Val Ala Tyr Thr Phe
290                 295                 300

Asp Ala Gly Pro Asn Ala Val Ile Phe Thr Leu Asp Asp Thr Val Ala
305                 310                 315                 320

Glu Phe Val Ala Ala Val Trp His Gly Phe Pro Pro Gly Ser Asn Gly
                325                 330                 335

Asp Thr Phe Leu Lys Gly Leu Gln Val Arg Pro Ala Pro Leu Ser Ala
            340                 345                 350

Glu Leu Gln Ala Ala Leu Ala Met Glu Pro Thr Pro Gly Gly Val Lys
        355                 360                 365

Tyr Ile Ile Val Thr Gln Val Gly Pro Gly Pro Gln Ile Leu Asp Asp
370                 375                 380

Pro Cys Ala His Leu Leu Gly Pro Asp Gly Leu Pro Lys Pro Ala Ala
385                 390                 395                 400

<210> SEQ ID NO 9
<211> LENGTH: 319
<212> TYPE: PRT
<213> ORGANISM: Lactobacillus delbrueckii

<400> SEQUENCE: 9

Met Ser Lys Thr Ala Arg Ala His Thr Asn Ile Ala Leu Ile Lys Tyr
1               5                   10                  15

Trp Gly Lys Lys Asp Ala Lys Leu Arg Leu Pro Leu Met Ser Ser Leu
            20                  25                  30

Ser Met Thr Leu Asp Ala Phe Tyr Ser Asp Thr Lys Ile Ser Asp Ser
        35                  40                  45

Glu Gln Met Ser Phe Lys Leu Asn Gly Gln Ala Val Ser Gly Pro Ala
    50                  55                  60

Ala Asp Arg Val Phe Ala Tyr Leu Arg Ala Met Gln Asp Arg Phe Gly
65                  70                  75                  80

Val Lys Gly Asn Leu Ala Val Glu Ser Val Asn Gln Val Pro Thr Ala
                85                  90                  95

Ala Gly Leu Ala Ser Ser Ser Ala Phe Ala Ala Met Ala Ala Ala
            100                 105                 110

Phe Ala Asp His Tyr Gln Leu Gly Val Asp Arg Gln Glu Leu Ser Arg
        115                 120                 125

Met Ala Arg Met Gly Ser Gly Ser Ala Ser Arg Ser Val Phe Gly Gly
    130                 135                 140

Phe Ser Val Trp Gln Lys Gly Asp Ser Asp Gln Thr Ser Tyr Ala Tyr
145                 150                 155                 160

Pro Leu Asp Glu Glu Pro Asp Met Asp Leu Arg Leu Leu Ala Val Glu
                165                 170                 175

Ile Asn Asp Gln Glu Lys Lys Ile Ser Ser Thr Lys Gly Met Glu Met
```

180                 185                 190
Ser Lys Ser Ser Pro Phe Tyr Gln Val Trp Leu Asp Arg Asn Asp Ser
                    195                 200                 205

Glu Ile Lys Glu Met Glu Ala Ile Lys Gln Ala Asp Phe Ser Lys
    210                 215                 220

Leu Gly Ser Leu Ala Glu Leu Asn Ala Ser Glu Met His Thr Leu Thr
225                 230                 235                 240

Phe Thr Ala Val Pro Gly Phe Thr Tyr Phe Glu Pro Asn Thr Ile Lys
                245                 250                 255

Ala Ile Lys Leu Val Gln Asp Leu Arg Gln Gln Gly Leu Glu Cys Tyr
                260                 265                 270

Tyr Thr Ile Asp Ala Gly Pro Asn Val Lys Val Leu Cys Gln Gly Lys
                275                 280                 285

Asn Ser Lys Asp Ile Ile Asn Cys Phe Glu Ser Ser Phe Asp Arg Val
                290                 295                 300

Lys Ile Ile Glu Ala Gly Phe Gly Pro Gly Val Thr Leu Leu Asp
305                 310                 315

<210> SEQ ID NO 10
<211> LENGTH: 317
<212> TYPE: PRT
<213> ORGANISM: Streptococcus mitis (strain B6)

<400> SEQUENCE: 10

Met Asp Arg Glu Pro Val Thr Val Arg Ser Tyr Ala Asn Ile Ala Ile
1               5                   10                  15

Ile Lys Tyr Trp Gly Lys Lys Glu Lys Met Val Pro Ala Thr
                20                  25                  30

Ser Ser Ile Ser Leu Thr Leu Glu Asn Met Tyr Thr Glu Thr Thr Leu
            35                  40                  45

Ser Ser Leu Pro Thr Asp Ala Thr Ala Asp Ala Phe Tyr Ile Asn Gly
        50                  55                  60

Gln Leu Gln Asn Glu Ala Glu His Val Lys Met Ser Lys Ile Ile Asp
65              70                  75                  80

Arg Tyr Arg Pro Asp Gly Asp Gly Phe Val Arg Ile Asp Thr Gln Asn
                85                  90                  95

Ser Met Pro Thr Ala Ala Gly Leu Ser Ser Ser Ser Ser Gly Leu Ser
            100                 105                 110

Ala Leu Val Lys Ala Cys Asn Ala Tyr Phe Lys Leu Gly Leu Asn Arg
        115                 120                 125

Ser Gln Leu Ala Gln Glu Ala Lys Phe Ala Ser Gly Ser Ser Ser Arg
    130                 135                 140

Ser Phe Tyr Gly Pro Leu Gly Ala Trp Asp Lys Asp Ser Gly Glu Ile
145                 150                 155                 160

Tyr Pro Val Glu Thr Gly Leu Lys Leu Ala Met Ile Met Leu Val Leu
                165                 170                 175

Glu Asp Lys Lys Lys Pro Ile Ser Ser Arg Asp Gly Met Lys Leu Cys
            180                 185                 190

Val Glu Thr Ser Thr Thr Phe Asp Asp Trp Val Arg Gln Ser Glu Lys
        195                 200                 205

Asp Tyr Gln Asp Met Leu Val Tyr Leu Lys Ala Asn Asp Phe Ala Lys
    210                 215                 220

Val Gly Glu Leu Thr Glu Lys Asn Ala Leu Ala Met His Ala Thr Thr
225                 230                 235                 240

```
Lys Thr Ala Ser Pro Ala Phe Ser Tyr Leu Thr Asp Ala Ser Tyr Glu
                245                 250                 255

Ala Met Asp Phe Val Arg Gln Leu Arg Glu Gln Gly Glu Ala Cys Tyr
            260                 265                 270

Phe Thr Met Asp Ala Gly Pro Asn Val Lys Val Leu Cys Gln Glu Lys
            275                 280                 285

Asp Leu Glu His Leu Ser Glu Ile Phe Gly Arg Tyr Arg Leu Ile
        290                 295                 300

Val Ser Lys Thr Lys Asp Leu Ser Gln Asp Gly Cys Cys
305                 310                 315

<210> SEQ ID NO 11
<211> LENGTH: 316
<212> TYPE: PRT
<213> ORGANISM: Streptococcus gallolyticus UCN34

<400> SEQUENCE: 11

Met Asp Arg Lys Ile Val Thr Val Lys Ser Tyr Ala Asn Ile Ala Ile
1               5                   10                  15

Ile Lys Tyr Trp Gly Lys Ala Asp Ala Val Lys Met Ile Pro Ala Thr
            20                  25                  30

Ser Ser Ile Ser Leu Thr Leu Glu Asn Met Phe Thr Thr Thr Thr Val
        35                  40                  45

Ser Phe Leu Pro Gln Ser Val Gly His Asp Glu Phe Tyr Ile Asn Gly
    50                  55                  60

Val Leu Gln Asp Glu Lys Glu His Ala Lys Ile Ser Ala Ile Ile Asp
65                  70                  75                  80

Gln Tyr Arg Gly Gly Arg Ser Glu Phe Val Lys Val Glu Thr Ser Asn
                85                  90                  95

Asn Met Pro Thr Ala Ala Gly Leu Ser Ser Ser Ser Gly Leu Ser
            100                 105                 110

Ala Leu Val Lys Ala Cys Asn Glu Leu Phe Glu Thr Gly Leu Asn Gln
            115                 120                 125

Ser Glu Leu Ala Gln Lys Ala Lys Phe Ala Ser Gly Ser Ser Ser Arg
    130                 135                 140

Ser Phe Phe Gly Pro Ile Ala Ala Trp Asp Lys Asp Ser Gly Asp Ile
145                 150                 155                 160

Tyr Pro Val Gln Thr Asp Leu Lys Leu Ala Met Ile Met Leu Val Leu
                165                 170                 175

Ser Asp Ser Lys Lys Pro Ile Ser Ser Arg Glu Gly Met Lys Arg Cys
            180                 185                 190

Ala Glu Thr Ser Thr Thr Phe Ala Asp Trp Val Lys Gln Ser Glu Gln
        195                 200                 205

Asp Tyr Lys Asp Met Leu Ala Tyr Leu Lys Ala Asn Asp Phe Glu Lys
    210                 215                 220

Val Gly Glu Leu Thr Glu Arg Asn Ala Leu Ala Met His Asp Thr Asn
225                 230                 235                 240

Thr His Ala Asn Pro Pro Phe Asn Tyr Leu Thr Asp Glu Thr Tyr Ala
                245                 250                 255

Ala Met Asp Phe Val Lys Ser Leu Arg Thr Gln Gly Glu Lys Cys Tyr
            260                 265                 270

Phe Thr Met Asp Ala Gly Pro Asn Val Lys Val Leu Cys Leu Glu Glu
            275                 280                 285

Asp Leu Glu Cys Leu Thr Lys Arg Phe Glu Glu Asn Tyr Arg Val Ile
    290                 295                 300
```

```
Ala Ser Arg Thr Lys Val Leu Pro Asp Glu Asn Asp
305                 310                 315

<210> SEQ ID NO 12
<211> LENGTH: 315
<212> TYPE: PRT
<213> ORGANISM: Streptococcus sanguinis SK36

<400> SEQUENCE: 12

Met Asp Arg Lys Pro Val Ser Val Lys Ser Tyr Ala Asn Ile Ala Ile
1               5                   10                  15

Val Lys Tyr Trp Gly Lys Lys Asp Ala Glu Lys Met Ile Pro Ser Thr
            20                  25                  30

Ser Ser Ile Ser Leu Thr Leu Glu Asn Met Tyr Thr Glu Thr Gln Leu
        35                  40                  45

Ser Pro Leu Pro Asp Thr Ala Thr Gly Asp Glu Phe Tyr Ile Asp Ser
    50                  55                  60

Gln Leu Gln Ser Pro Ala Glu His Ala Lys Ile Ser Lys Ile Ile Asp
65                  70                  75                  80

Arg Phe Arg Ser Pro Glu Asp Gly Phe Val Arg Val Asp Thr Ser Asn
                85                  90                  95

Asn Met Pro Thr Ala Ala Gly Leu Ser Ser Ser Ser Gly Leu Ser
            100                 105                 110

Ala Leu Val Lys Ala Cys Asn Ala Tyr Phe Gln Thr Gly Tyr Gln Thr
            115                 120                 125

Gln Glu Leu Ala Gln Leu Ala Lys Phe Ala Ser Gly Ser Ser Ala Arg
        130                 135                 140

Ser Phe Phe Gly Pro Leu Ala Ala Trp Asp Lys Asp Ser Gly Ala Ile
145                 150                 155                 160

Tyr Pro Val Lys Thr Asp Leu Lys Leu Ala Met Ile Met Leu Val Leu
                165                 170                 175

His Asp Glu Lys Lys Pro Ile Ser Ser Arg Asp Gly Met Glu Leu Cys
            180                 185                 190

Ala Lys Thr Ser Thr Ile Phe Pro Asp Trp Ile Ala Gln Ser Ala Leu
        195                 200                 205

Asp Tyr Lys Ala Met Leu Ser Tyr Leu Gln Asp Asn Asp Phe Ala Lys
    210                 215                 220

Val Gly Gln Leu Thr Glu Glu Asn Ala Leu Arg Met His Ala Thr Thr
225                 230                 235                 240

Glu Lys Ala Tyr Pro Pro Phe Ser Tyr Leu Thr Glu Glu Ser Tyr Gln
                245                 250                 255

Ala Met Asp Ala Val Arg Lys Leu Arg Glu Gln Gly Glu Arg Cys Tyr
            260                 265                 270

Phe Thr Met Asp Ala Gly Pro Asn Val Lys Val Leu Cys Leu Glu Glu
        275                 280                 285

Asp Leu Asp His Leu Val Ala Ile Phe Glu Lys Asp Tyr Arg Leu Ile
    290                 295                 300

Val Ser Lys Thr Lys Asp Leu Ser Asp Glu Asp
305                 310                 315

<210> SEQ ID NO 13
<211> LENGTH: 317
<212> TYPE: PRT
<213> ORGANISM: Streptococcus sp. M143

<400> SEQUENCE: 13
```

```
Met Asp Arg Lys Pro Val Thr Val Arg Ser Tyr Ala Asn Ile Ala Ile
1               5                   10                  15

Ile Lys Tyr Trp Gly Lys Lys Lys Glu Lys Met Val Pro Ala Thr
            20                  25                  30

Ser Ser Ile Ser Leu Thr Leu Glu Asn Met Tyr Thr Glu Thr Thr Leu
            35                  40                  45

Ser Pro Leu Pro Thr Asp Ala Thr Ala Asp Ala Phe Tyr Ile Asn Gly
50                  55                  60

Gln Leu Gln Ser Glu Ala Glu His Ala Lys Met Ser Lys Ile Ile Asp
65                  70                  75                  80

Arg Tyr Arg Pro Ala Gly Glu Gly Phe Val Arg Ile Asp Thr Gln Asn
                85                  90                  95

Asn Met Pro Thr Ala Ala Gly Leu Ser Ser Ser Ser Gly Leu Ser
                100                 105                 110

Ala Leu Val Lys Ala Cys Asn Ala Tyr Phe Gln Leu Gly Leu Asn Arg
            115                 120                 125

Ser Gln Leu Ala Gln Glu Ala Lys Phe Ala Ser Gly Ser Ser Ser Arg
            130                 135                 140

Ser Phe Tyr Gly Pro Leu Gly Ala Trp Asp Lys Asp Ser Gly Glu Ile
145                 150                 155                 160

Tyr Pro Val Glu Thr Asp Leu Lys Leu Ala Met Ile Met Leu Val Leu
                165                 170                 175

Glu Asp Lys Lys Lys Pro Ile Ser Ser Arg Asp Gly Met Lys Leu Cys
            180                 185                 190

Val Glu Thr Ser Thr Thr Phe Asp Asp Trp Val Arg Gln Ser Glu Lys
            195                 200                 205

Asp Tyr Gln Asp Met Leu Leu Tyr Leu Lys Glu Asn Asp Phe Ala Lys
            210                 215                 220

Val Gly Glu Leu Thr Glu Lys Asn Ala Leu Ala Met His Ala Thr Thr
225                 230                 235                 240

Lys Thr Ala Ser Pro Ala Phe Ser Tyr Leu Thr Asp Ala Ser Tyr Glu
                245                 250                 255

Ala Met Asp Phe Val Arg Gln Leu Arg Glu Gly Gly Ser Cys Tyr
            260                 265                 270

Phe Thr Met Asp Ala Gly Pro Asn Val Lys Val Leu Cys Gln Glu Glu
            275                 280                 285

Asp Leu Glu His Leu Ser Glu Ile Phe Gly Gln Arg Tyr Arg Leu Ile
            290                 295                 300

Val Ser Lys Thr Lys Asp Leu Ser Gln Asp Asp Cys Cys
305                 310                 315

<210> SEQ ID NO 14
<211> LENGTH: 341
<212> TYPE: PRT
<213> ORGANISM: Streptococcus suis 89/1591

<400> SEQUENCE: 14

Met Thr Lys Gln Ile Gly Ile Ala Arg Ala His Thr Asn Ile Ala Leu
1               5                   10                  15

Ile Lys Tyr Trp Gly Lys Arg Asp Lys Glu Leu Phe Leu Pro Met Asn
            20                  25                  30

Ser Ser Leu Ser Leu Thr Leu Asp Ala Phe Tyr Thr Asp Thr Lys Val
            35                  40                  45

Val Phe Asp Pro Glu Leu Thr Ala Asp Glu Phe Tyr Leu Asn Gly Met
```

```
                 50                  55                  60
Leu Gln Lys Glu Lys Glu Ile Leu Lys Ile Ser Arg Phe Leu Asp Leu
 65                  70                  75                  80

Phe Cys Glu Tyr Ile Gly Glu Arg Ala Phe Ala Arg Val Glu Ser Leu
                 85                  90                  95

Asn Phe Val Pro Thr Ala Ala Gly Leu Ala Ser Ala Ser Ala Phe
                100                 105                 110

Ala Ala Leu Ala Leu Ala Thr Ala Thr Ala Leu Asp Leu Asp Leu Ser
                115                 120                 125

Pro Ala Thr Leu Ser Thr Leu Ala Arg Arg Gly Ser Gly Ser Ser Thr
                130                 135                 140

Arg Ser Leu Phe Gly Gly Phe Val Glu Trp Asp Met Gly Thr Gly Ser
145                 150                 155                 160

Glu Asp Ser Met Ala His Pro Ile Asp Asp Ala Asp Trp Asp Ile Gly
                165                 170                 175

Met Val Val Leu Ala Val Asn Thr Gly Pro Lys Lys Ile Ala Ser Arg
                180                 185                 190

Glu Gly Met Asp His Thr Val Ala Thr Ser Pro Phe Tyr Ser Ala Trp
                195                 200                 205

Val Asp Thr Ala Lys Gln Asp Leu Ala Asp Ile Lys Ala Ala Ile Ala
                210                 215                 220

Gly Arg Asp Phe Glu Lys Leu Gly Gln Ile Thr Glu His Asn Gly Met
225                 230                 235                 240

Lys Met His Ala Thr Thr Leu Ser Ala Asn Pro Pro Phe Thr Tyr Trp
                245                 250                 255

Ser Ala Asp Ser Leu Val Ala Gln Glu Ala Val Arg Gln Val Arg Glu
                260                 265                 270

Ala Thr Gly Leu Ser Ala Tyr Met Thr Met Asp Ala Gly Pro Asn Val
                275                 280                 285

Lys Val Leu Cys Arg Ala Ser Gln Met Asp Glu Leu Val Ala Glu Leu
                290                 295                 300

Ala Lys Val Phe Pro Arg Glu Lys Ile Ile Thr Ser Lys Pro Gly Pro
305                 310                 315                 320

Ala Ala Tyr Val Leu Ser Glu Asp Glu Trp Gln Thr Ser Gln Ala Ala
                325                 330                 335

Phe Glu Lys Gly Leu
                340

<210> SEQ ID NO 15
<211> LENGTH: 314
<212> TYPE: PRT
<213> ORGANISM: Streptococcus salivarius SK126

<400> SEQUENCE: 15

Met Asp Arg Lys Pro Val Ser Val Lys Ser Tyr Ala Asn Ile Ala Ile
  1               5                  10                  15

Val Lys Tyr Trp Gly Lys Ala Asp Ala Glu Arg Met Ile Pro Ser Thr
                 20                  25                  30

Ser Ser Ile Ser Leu Thr Leu Glu Asn Met Tyr Thr Glu Thr Lys Leu
                 35                  40                  45

Ser Phe Leu Pro Glu Asp Ala Thr Gly Asp Val Met Tyr Ile Asp Asp
                 50                  55                  60

Glu Leu Gln Gly Glu Lys Glu Thr Thr Lys Ala Ser Lys Val Leu Asp
 65                  70                  75                  80
```

```
Leu Phe Arg Asn Asn Ser Asn Gln His Val Lys Ile Glu Thr Trp Asn
                85                  90                  95

Asn Met Pro Thr Ala Ala Gly Leu Ser Ser Ser Ser Gly Leu Ser
            100                 105                 110

Ala Leu Val Lys Ala Ala Asn Glu Leu Phe Gln Val Gly Lys Thr Gln
            115                 120                 125

Ser Glu Leu Ala Gln Ile Ala Lys Phe Ala Ser Gly Ser Ser Arg
130                     135                 140

Ser Phe Phe Gly Pro Leu Ala Ala Trp Asp Lys Asp Ser Gly Glu Val
145                 150                 155                 160

Tyr Pro Val Glu Thr Asp Leu Lys Leu Ala Met Ile Met Leu Val Leu
                165                 170                 175

Thr Asp Gln Lys Lys Pro Val Ser Ser Arg Asp Gly Met Lys Leu Cys
            180                 185                 190

Thr Glu Thr Ser Thr Ser Phe Pro Glu Trp Ile Lys Gln Ser Glu Leu
            195                 200                 205

Asp Tyr Lys Asp Met Leu Ala Tyr Leu Lys Ala Asn Asp Phe Gln Ala
            210                 215                 220

Val Gly Glu Leu Thr Glu Ala Asn Ala Leu Arg Met His Gln Thr Thr
225                 230                 235                 240

Ser Thr Ala Asn Pro Pro Phe Ser Tyr Leu Thr Glu Ala Ser Tyr Gln
            245                 250                 255

Ala Met Asp Lys Val Lys Ala Leu Arg Ala Ser Gly Glu Gln Cys Tyr
            260                 265                 270

Phe Thr Met Asp Ala Gly Pro Asn Val Lys Val Leu Cys Leu Glu Glu
            275                 280                 285

Asp Leu Asp Arg Leu Ala Glu His Phe Arg Lys Asp Tyr Gln Val Ile
            290                 295                 300

Val Ser Arg Thr Lys Glu Leu Pro Asp Ala
305                 310
```